US009546247B2

(12) United States Patent
Lei et al.

(10) Patent No.: US 9,546,247 B2
(45) Date of Patent: Jan. 17, 2017

(54) EXPLOSIVE DETECTION POLYMER COMPRISING FUNCTIONALIZED POLYAMINE POLYMERS AND METHODS OF USING THE SAME

(71) Applicant: University of Connecticut, Farmington, CT (US)

(72) Inventors: Yu Lei, Mansfield Center, CT (US); Ying Wang, Willington, CT (US)

(73) Assignee: University of Connecticut, Farmington, CT (US)

( * ) Notice: Subject to any disclaimer, the term of this patent is extended or adjusted under 35 U.S.C. 154(b) by 135 days.

(21) Appl. No.: 14/386,198

(22) PCT Filed: Mar. 21, 2013

(86) PCT No.: PCT/US2013/033331
§ 371 (c)(1),
(2) Date: Sep. 18, 2014

(87) PCT Pub. No.: WO2013/165625
PCT Pub. Date: Nov. 7, 2013

(65) Prior Publication Data
US 2015/0056711 A1 Feb. 26, 2015

Related U.S. Application Data

(60) Provisional application No. 61/613,655, filed on Mar. 21, 2012.

(51) Int. Cl.
*C08G 73/02* (2006.01)
*G01N 33/18* (2006.01)
*G01N 33/22* (2006.01)
*G01N 21/64* (2006.01)

(52) U.S. Cl.
CPC ....... *C08G 73/0206* (2013.01); *C08G 73/0213* (2013.01); *G01N 21/6428* (2013.01); *G01N 33/1826* (2013.01); *G01N 33/227* (2013.01); *G01N 21/643* (2013.01); *Y10T 436/147777* (2015.01); *Y10T 436/170769* (2015.01); *Y10T 436/173076* (2015.01)

(58) Field of Classification Search
CPC . C08G 73/0206; C08G 73/0213; G01N 33/22; G01N 33/227; G01N 33/1826; G01N 21/64; G01N 21/6428; G01N 21/643; G01N 21/6447; G01N 2021/6432; Y10T 436/14; Y10T 436/145555; Y10T 436/147777; Y10T 436/17; Y10T 436/170769; Y10T 436/173076; Y10T 436/173845
USPC ..... 436/91, 96, 98, 106, 107, 110, 111, 164, 436/166, 172; 422/82.05, 82.08; 525/417
See application file for complete search history.

(56) References Cited

U.S. PATENT DOCUMENTS

| 7,208,122 | B2 | 4/2007 | Swager et al. |
| 7,393,503 | B2 | 7/2008 | Swager et al. |
| 7,662,309 | B2 | 2/2010 | Swager et al. |
| 7,927,881 | B2 | 4/2011 | Trogler et al. |
| 8,765,483 | B2 * | 7/2014 | Lei ........................ G01N 21/643 422/82.08 |
| 2007/0269900 | A1 * | 11/2007 | Lebret ................... G01N 27/126 436/107 |
| 2008/0242870 | A1 | 10/2008 | Meador et al. |
| 2009/0233374 | A1 * | 9/2009 | Zang ................... G01N 21/6428 436/106 |

OTHER PUBLICATIONS

Zhang et al. Journal of the American Chemical Society, vol. 133, May 12, 2011, pp. 8424-8427.*
Burattini, et al., Pyrene-Functionalised, Alternating Copolyimide for Sensing Nitroaromatic Compounds, Macromolecular Rapid Communications, vol. 30, No. 6, pp. 459-463, 2009, See Abstract; Scheme 1; Figure 1.
Long, et al., Electrospun Nanofibrous Film Doped With a Conjugated Polymer for DNT Fluorescence Sensor, Macromolecules, vol. 42, No. 17, pp. 6501-6509, 2009, See Abstract and Scheme 1.
Du, et al, Preparation of Pyrene-Functionalized Fluorescent Film With a Benzene Ring in Spacer and Sensitive Detection to Pieric Acid in Aqueous Phase, Journal of Photochemistry and Photobiology A; Chemistry, 2011, vol. 217, No. 2, pp. 356-362., see abstract; Scheme 1; Figure 7.
He, et al., Pyrene-Containing Conjugated Polymer-Based Fluorescent Films for Highly Sensitive and Selective Sensitive and Selective Sensing of TNT in Aqueous Medium, Macromolecules, vol. 44, No. 12, pp. 4759-4766, 2011, see abstract; Scheme 1; Figure 4.
Wang, et al., FRET and PET-Based Sensing in a Single Material: Expanding the Dynamic Range fo an Ultra-Sensitive Nitroaromatic Explosives Assay, Chemical Communications, vol. 48, No. 79, pp. 9903-9905, Aug. 20, 2012.
PCT International Search Report and Written Opinion of PCT/US2013/033331 dated Dec. 5, 2013.
Cline, G.W. et al., The Aminolysis of N-Hydroxysuccinimide Esters—A Structure Reactivity Study, Journal of the American Chemical Society, 1987, 109(10): pp. 3087-3091.
Cline, G.W. et al., Kinetics and Mechanisms of the Aminolysis of N-Hydroxysuccinimide Esters in Aqueous Buffers, Journal of Organic Chemistry, 1988, 53(15): pp. 3583-3586.
Shankaran, D.R. et al., Surface plasmon resonance immunosensor for highly sensitive detection of 2,4,6-trinitrotoluene, Biosensors & Bioelectronics, 2005, 20(9): pp. 1750-1756.

(Continued)

*Primary Examiner* — Maureen Wallenhorst
(74) *Attorney, Agent, or Firm* — McCarter & English, LLP

(57) ABSTRACT

Explosives detection polymers are provided that include a polyamine polymer, such as polyethylenimine, functionalized with a small molecule fluorophore. Methods for detecting an explosive material using polyamine polymers functionalized with a small molecule fluorophore are also provided. Sensors for explosive detection are provided that include a polyamine polymer functionalized with a small molecule fluorophore and a complementary analytical device.

22 Claims, 12 Drawing Sheets

(56) References Cited

OTHER PUBLICATIONS

Walker, N.R. et al., Selective detection of gas-phase TNT by integrated optical waveguide spectrometry using molecularly imprinted sol-gel sensing films, Analytica Chimica Acta, 2007, 593(1): pp. 82-91.

Gao, D.M. et al., Resonance Energy Transfer-Amplifying Fluorescence Quenching at the Surface of Silica Nanoparticles toward Ultrasensitive Detection of TNT, Analytical Chemistry, 2008, 80(22): pp. 8545-8553.

Dasary, S.S.R. et al., Gold Nanoparticle Based Label-Free SERS Probe for Ultrasensitive and Selective Detection of Trinitrotoluene, Journal of the American Chemical Society, 2009, 131(38): pp. 13806-13812.

Fang, Q.L. et al., Inverted Opal Fluorescent Film Chemosensor for the Detection of Explosive Nitroaromatic Vapors through Fluorescence Resonance Energy Transfer, Chemistry—A European Journal, 2009, 15(43): pp. 11507-11514.

Germain, M.E. et al., Optical explosives detection: from color changes to fluorescence turn-on, Chemical Society Reviews, 2009, 38(9): pp. 2543-2555.

Chen, W. et al., Pyrene-Functionalized Ruthenium Nanoparticles as Effective Chemosensors for Nitroaromatic Derivatives, Analytical Chemistry, 2010, 82(2): pp. 461-465.

Chen, Y.F. et al., L-cysteine-capped CdTe QD-based sensor for simple and selective detection of trinitrotoluene, Nanotechnology, 2010, 21(12).

Geng, J.L. et al., A Reversible Dual-Response Fluorescence Switch for the Detection of Multiple Analytes, Chemistry—A European Journal, 2010, 16(12): pp. 3720-3727.

Lee, Y.H. et al., Dipyrenylcalix[4]arene—A Fluorescence-Based Chemosensor for Trinitroaromatic Explosives, Chemistry—A European Journal, 2010, 16(20): pp. 5895-5901.

Qu, W.G. et al., Plasmonic resonance energy transfer-based nanospectroscopy for sensitive and selective detection of 2, 4, 6-trinitrotoluene (TNT), Chemical Communications, 2011, 47(4): pp. 1237-1239.

Xu, B.W. et al., Selective Detection of TNT and Picric Acid by Conjugated Polymer Film Sensors with Donor-Acceptor Architecture, Macromolecules, 2011, 44(13): pp. 5089-5092.

PCT/US2013/033331, Mar. 21, 2013, WO 2013/165625.

U.S. Appl. No. 61/613,655, filed Mar. 21, 2012.

\* cited by examiner

EXPLOSIVE DETECTION POLYMER COMPRISING FUNCTIONALIZED POLYAMINE POLYMERS AND METHODS OF USING THE SAME

CROSS-REFERENCE TO RELATED APPLICATION(S)

The present application claims priority benefit to a provisional patent application entitled "Explosives Detection Polymer Comprising Functionalized Polyamine Polymers and Methods of Using the Same," which was filed on Mar. 21, 2012, and assigned Ser. No. 61/613,655. The entire content of the foregoing provisional application is incorporated herein by reference.

STATEMENT REGARDING FEDERALLY SPONSORED RESEARCH OR DEVELOPMENT

This invention was made with Government support under Grant No. CMMI 0730826 and IIP 1157650 from the National Science Foundation (NSF) and under Grant No. 2008-ST-108-000005 from the Department of Homeland Security (DHS). The Government has certain rights in the invention.

BACKGROUND OF THE INVENTION

Low level explosives detection in aqueous environments is challenging, in part, because the solubility of most explosives is low and saturation concentrations are hardly ever reached in open waters due to dilution. Nitroaromatic compounds (NACs), including trinitrotoluene (TNT), dinitrotoluene (DNT), and trinitrophenyl-methylnitramine (Tetryl), are the most common explosives and those which are most often found in aqueous environments. Currently, these compounds are detected using US EPA protocol SW-846 Method 8330 which involves reverse-phase HPLC with UV detection, chemiluminescence, spectrophotometric assays, immunosensors, surface enhanced Raman scattering and electrochemical methods. The current methodology, however, does not provide the required selectivity or sensitivity needed to detect these explosives, and others, at ultra low levels.

Fluorescence quenching methods, owing to their relatively low cost, efficiency, portability, high sensitivity, and ease of operation, have emerged as a preferred means of detecting NAC explosives. It is believed that the electron-deficient NACs bind to electron-rich fluorescent materials and result in fluorescence quenching by a photoinduced electron transfer (PET) mechanism. In the past decades, a wide range of small molecule fluorophores and conjugated polymers have been developed for effective NAC sensing, but most of them are applied to detect explosives either in vapor/solid phase or in organic solvents, not in aqueous environments. Moreover, the quenching of fluorophores may be interfered with by other electron-deficient compounds.

Thus, there remains a need for selective detection methods capable of detecting low levels of explosives in aqueous environments.

SUMMARY OF THE INVENTION

The present disclosure is directed, in part, to polymers and methods for quick, inexpensive and highly sensitive explosives detection, which are capable of detecting a wide range of explosive materials. The explosives detection polymers of the present disclosure are based on polyamine polymers functionalized to include small molecule fluorophores. The polymers are highly sensitive to the presence of explosives, possibly due to dual and sequential quenching mechanisms, i.e. latent Förster resonance energy transfer (FRET) followed by photoinduced electron transfer (PET). Moreover, the polymers and methods of the present disclosure are, as discussed in more detail herein, highly effective in detecting levels of explosives, such as TNT and Tetryl.

Accordingly, in some embodiments, the present disclosure provides explosives detecting polymers. Such polymers include a polyamine polymer functionalized with a small molecule fluorophore. The polyamine polymer may include, for example, a linear or branched, polyethylenimine, polyvinylamine, polyallylamine, polylysine or mixtures thereof. The small molecule fluorophore may include, for example, an aromatic multi-ring hydrocarbon, an aromatic multi-ring heterocycle, or a mixture thereof.

In some embodiments, the polyamine polymer functionalized with a small molecule fluorophore may include, for example, a plurality of structural units corresponding to Formula (I):

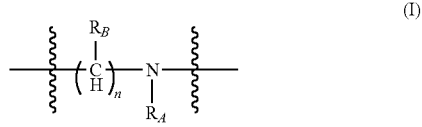

(I)

wherein each $R_A$ is selected independently from the group consisting of hydrogen, Formula (II) and Formula (III):

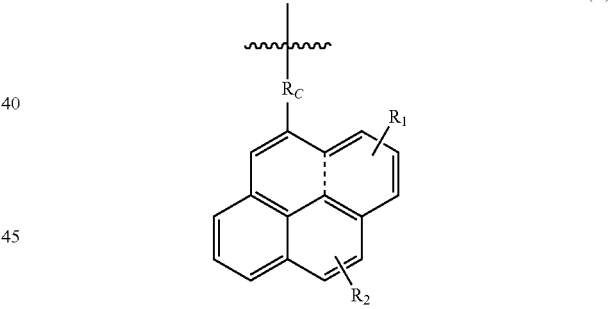

(II)

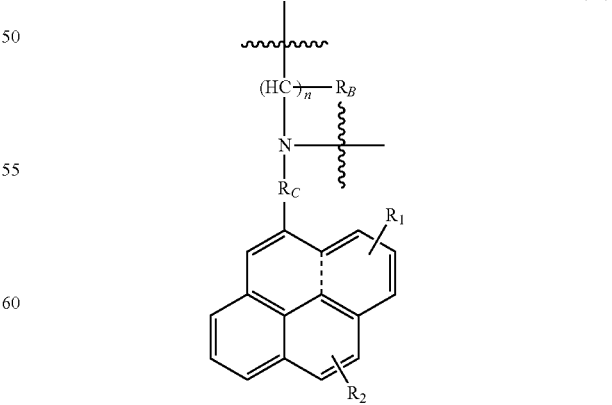

(III)

wherein each $R_C$ is selected independently from the group consisting of hydrogen and $-C(O)-C_{2-6}$ alkyl-;

wherein $R_1$ and $R_2$ are each independently selected from hydrogen, cyano, $C_{1-4}$ alkyl, —B(OH)$_2$, —C(O)H, —$C_{1-4}$ alkyl-C(O)H, —C(O)CH$_3$, —$C_{1-4}$ alkyl-C(O)CH$_3$, —C(O)OH, —$C_{1-4}$ alkyl-C(O)OH, —C(O)OCH$_3$, —$C_{1-4}$ alkyl-C(O)OCH$_3$ and —$C_{1-4}$ alkyl-C(O)O-succinimide;

$R_B$ is selected from the group consisting of a bond, hydrogen, amine and $C_1$-$C_3$ alkyl;

and each n is selected independently from 2-8.

In some embodiments, the small molecule fluorophore is selected from pyrene, 1-pyrenebutyric acid, pyrene-1-boronic acid, 1-pyrenebutyric acid N-hydroxysuccinimide ester, and mixtures thereof. In other embodiments, the small molecule fluorophore comprises pyrene.

In some embodiments, the polymer comprises a branched polyethylenimine functionalized with 1-pyrenebutyric acid.

In some embodiments, the small molecule fluorophore is substantially evenly distributed throughout the polymer. The small molecule fluorophore may be present on the polyamine polymer at about 1% to about 60%, by molar ratio of pyrene to primary amine. In other embodiments, the polymer is capable of detecting an explosive material in an amount less than about 1000 ppm (e.g. less than about 0.033 ppb). In some embodiments, the polymer is capable of detecting an explosive material in less than about 6 minutes.

In some embodiments, the present disclosure provides methods for detecting an explosive material. Such methods may generally include contacting the explosives detecting polymer described herein with an explosive material for at least about 1 second; measuring the amount of fluorescence emitted by the explosives detecting polymer; and comparing the amount of fluorescence with a suitable control. An explosive material can be detected where the fluorescence of the explosives detecting polymer is less than the fluorescence of the suitable control.

The explosive material that may be detected using the polymers and methods of the present disclosure include, for example, octahydro-1,3,5,7-tetranitro-1,3,5,7-tetrazocine (HMX), hexahydro-1,3,5-trinitro-1,3,5-triazine (RDX), 1,3,5-trinitrobenzene (TNB), 1,3-dinitrobenzene (DNB), methyl-2,4,6-trinitrophenylnitramine (Tetryl), nitrobenzene (NB), 2,4,6-trinitrotoluene (TNT), picric acid (PA), 2,4-dinitrotoluene (24DNT), 2,6-dinitrotoluene (26DNT), o-nitrotoluene (2NT), m-nitrotoluene (3NT), p-nitrotoluene (4NT), nitroglycerin (NG), 4-amino-2,6-dinitrotoluene (4-Am-DNT), 2-amino-4,6-dinitrotoluene (2-Am-DNT), pentaerythritol tetranitrate (PETN) and 2,3-dimethyl-2,3-dinitrobutane (DMNB).

In some embodiments, the method is capable of detecting an explosive material in an amount less than about 1000 ppm. In some embodiments, the method is capable of detecting an explosive material in an amount less than about 0.033 ppb.

In some embodiments, the explosive material comprises Tetryl. In some embodiments, the explosive material comprises TNT. In some embodiments, the explosive material comprises TNB. In some embodiments, the explosive material comprises dinitrotoluene. In some embodiments, the explosive material comprises DNB. In some embodiments, the explosive material comprises NB.

In some embodiments, measuring the amount of fluorescence emitted by the explosives detecting polymer comprises measurement of emission with a fluorimeter. In other embodiments, measuring the amount of fluorescence emitted by the explosives detection polymer comprises measurement of emission with a naked eye under UV light.

In some embodiments, the present disclosure provides methods for forming a polyamine polymer functionalized with a small molecule fluorophore. The method may comprise providing a polyamine polymer having a structure corresponding to Formula (I):

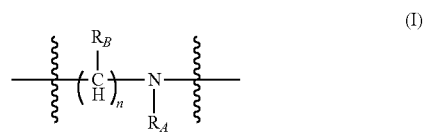

wherein each $R_A$ is selected independently from the group consisting of hydrogen and another repeating structure corresponding to Formula (I);

wherein $R_B$ is selected from the group consisting of a bond, hydrogen, amine and $C_1$-$C_3$ alkyl; and each n is selected independently from 2-8; and reacting the polyamine polymer with an ester having a structure corresponding to Formula (IV):

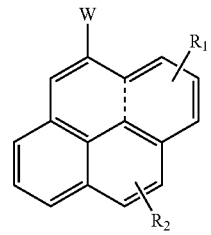

wherein W is —$C_{2-6}$ alkyl-C(O)-LG, wherein LG is a leaving group, wherein $R_1$ and $R_2$ are each independently selected from hydrogen, cyano, $C_{1-4}$ alkyl, —B(OH)$_2$, —C(O)H, —$C_{1-4}$ alkyl-C(O)H, —C(O)CH$_3$, —$C_{1-4}$ alkyl-C(O)CH$_3$, —C(O)OH, —$C_{1-4}$ alkyl-C(O)OH, —C(O)OCH$_3$, —$C_{1-4}$ alkyl-C(O)OCH$_3$ and —$C_{1-4}$ alkyl-C(O)O-succinimide;

wherein the polyamine functionalized with a small molecule fluorophore is formed.

In some embodiments, the present disclosure provides sensors which include the explosives detecting polymer described herein. In some embodiments, the sensor also includes a complementary analytical device, such as a fluorimeter, a mass spectrometer and/or an absorption spectrometer.

BRIEF DESCRIPTION OF THE FIGURES

FIG. 7a shows ultra-trace TNT analysis where the analyte concentrations from top to bottom are 0, 0.033, 0.164, 0.322, 0.643, 1.91, 3.44, 6.54, 18.8, 33.6, 63.7, 182.29, 327, 619, 1771, 3174, and 6014 ppb, respectively. FIG. 7b shows moderate to high concentration TNT analysis where the analyte concentrations from top to bottom are 6.014, 17.2, 30.9, 57.1, 81.9, 105, 128, 149, 169, 189, 207, and 225 ppm, respectively.

FIGS. 8a and 8c show regular plots. FIGS. 8b and 8d show semi-log plots. The inset shows enlarged plots for low TNT concentrations (0-10 ppm).

FIG. 9a shows a regular plot. FIG. 9b shows a semi-log plot. The inset shows enlarged plots for low TNT concentrations (0-10 ppm).

DETAILED DESCRIPTION OF THE INVENTION

The present disclosure provides polymers and methods for detecting explosive materials. The present disclosure may be based, at least in part, on dual and sequential quenching mechanisms, such as latent Förster resonance energy transfer (FRET) followed by photoinduced electron transfer (PET).

Figure 1:
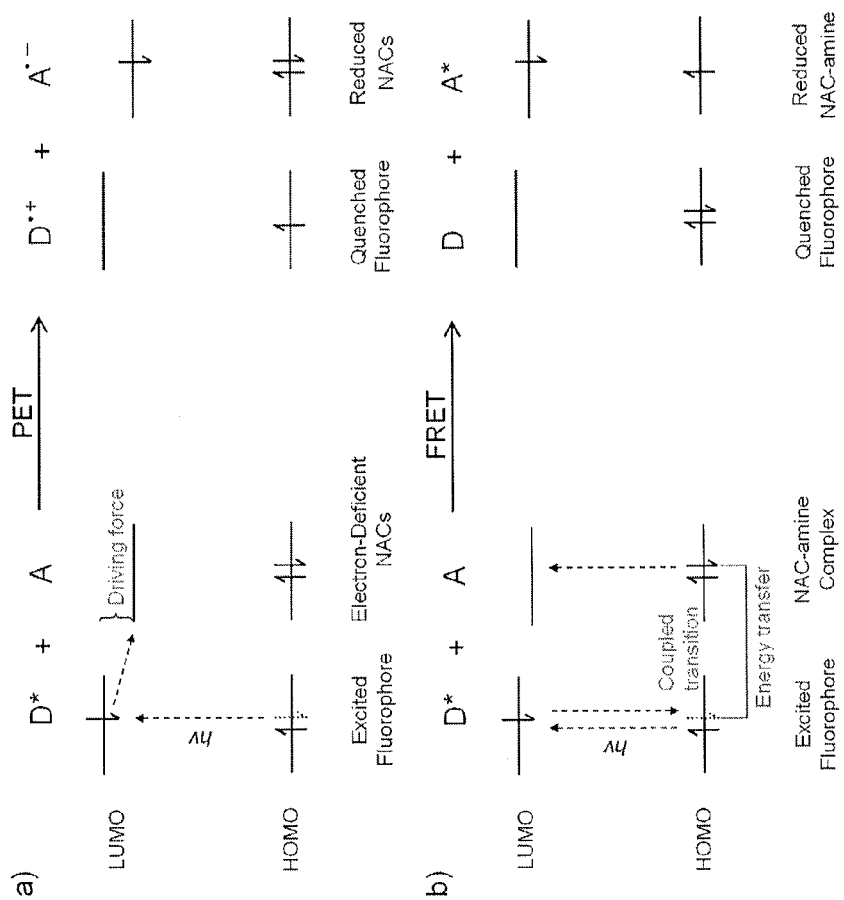
FIG. 1 shows a comparison between the photoinduced electron transfer (PET) process (FIG. 1a) and the Förster resonance energy transfer (FRET) process (FIG. 1b).

In this regard, and without wishing to be bound by any particular theory, it is believed that electron-rich amines may be used as an NAC binding site to form a colored adduct, or a Meisenheimer complex, with electron-deficient NACs. Moreover, these Meisenheimer complexes have strong absorption at ca. 500 nm and may be designed to couple with the emission spectra of chosen fluorophores to induce a Förster resonance energy transfer (FRET) process. Compared to the PET process, shown in FIG. 1a, FRET may be a more efficient and specific type of fluorescence quenching mechanism for nitroaromatic explosives, as shown in FIG. 1b. The energy from the fluorescent emission of a donor dye in FRET is transferred to an acceptor and simultaneously excites an electron to the excited state. This resonance energy transfer occurs without involving the conversion to thermal energy or any molecular collision, making it more efficient than PET process. Consequently, the quenching sensitivity could potentially be improved by several orders of magnitudes.

The present disclosure may also be based, at least in part, on the presence of co-facial interactions between the π-orbitals of the bound small molecule fluorophores. Such co-facial interactions are typically referred to as "π-π stacking" or "π-π interactions." By creating favorable π-π interactions (e.g. during derivatization and/or swelling-deswelling of the polymer) energy transfer between donor and acceptor species may be facilitated as well as long-range exciton migration along the polymer chain. This may increase not only the likelihood, but also the amplitude of quenching.

In some embodiments, the present disclosure is directed to a fluorescent polymer capable of dual and sequential quenching mechanisms, such as latent FRET at low NACs concentration followed by PET at high NACs concentration. These fluorescent polymers may be able to facilitate both an improved specific recognition with NACs and the amplification of FRET-based fluorescence quenching response in aqueous samples, as well as also achieve a broad dynamic detection range (e.g. spanning 7-orders of magnitude) for NACs through a FRET-PET combo quenching system.

The polymers, methods and sensors described herein may provide advantages over presently utilized methods, including, for example, mass-production with low cost, user-friendliness (e.g. only handheld UV light required), speed of quenching and detection. Moreover, polymers, methods and sensors of the present disclosure can be used alone with direct visualization (e.g. under UV light), or can be used in combination with any number of detection systems, such as those which employ fluorimetry, absorption spectroscopy, mass spectrometry and/or other methods known to those skilled in the art. Such combinations can, for example, further increase the sensitivity of the polymers, methods and sensors of the present invention.

Definitions

In order to more clearly and concisely describe the subject matter of the claims, the following definitions are intended to provide guidance as to the meaning of terms used herein.

As used herein, the articles "a" and "an" mean "one or more" or "at least one," unless otherwise indicated. That is, reference to any element of the present invention by the indefinite article "a" or "an" does not exclude the possibility that more than one of the element is present.

Certain values and ranges are recited in connection with various embodiments of the present invention. It is to be understood that all values and ranges which fall between the values and ranges listed are intended to be encompassed by the present invention unless explicitly stated otherwise.

The phrase "and/or," as used herein, should be understood to mean either or any combination of the elements recited. Other elements may optionally be present other than the elements specifically identified by the "and/or" clause, whether related or unrelated to those elements specifically identified unless clearly indicated to the contrary.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements.

As used herein, "alkyl" groups include saturated hydrocarbons having one or more carbon atoms, including straight-chain alkyl groups (e.g. methyl, ethyl, propyl, butyl, pentyl, hexyl, methylene, ethylene, propylene, butylene, pentylene, hexylene, etc.), branched-chain alkyl groups (isopropyl, tert-butyl, sec-butyl, isobutyl, etc.), and alkyl-substituted alkyl groups (e.g. alkyl-substituted cycloalkyl groups and cycloalkyl-substituted alkyl groups). The term "$C_{1-6}$" as in "$C_{1-6}$ alkyl" means alkyl groups containing 1 to 6 carbon atoms.

Explosives Detection Polymer

The present disclosure provides an explosives detection polymer. The polymer includes, for example, a polyamine polymer and a small molecule fluorophore. The small molecule may be covalently bonded to the polyamine polymer resulting in a polyamine polymer functionalized with a small molecule fluorophore.

As used herein, the term "polyamine" or "polyamine polymer" refers to a polymer having a plurality saturated or unsaturated, substituted or unsubstituted aminohydrocarbon units. For example, representative polyamine polymers include polyethylenimine (PEI), polyvinylamine, polyallylamine and polylysine.

In some embodiments, the polyamine polymer has a low background signal, substantially no background signal, or a background signal which does not substantially interfere with the signal generated by the fluorophore or the fluorophore within the explosives detection polymer, either in the presence or in the absence of analyte.

As used herein, the term "small molecule," when used in reference to the fluorophore, denotes a compound that may be covalently bound to a polymer and is not itself the product of polymerization, and has a low molecular weight (e.g. molecules having a molecular weight of less than about 2,000 Da). In some embodiments, small molecules have a molecular weight of less than about 1,500 Da. In other embodiments, small molecules have a molecular weight of less than about 1,000 Da. In still other embodiments, small molecules have a molecular weight of less than about 750 Da. In yet other embodiments, small molecules have a molecular weight of less than about 500 Da.

Although the small molecule fluorophore is not limited to macrocyclic compounds, in some embodiments, the small molecule fluorophore is an aromatic multi-ring hydrocarbon and/or an aromatic multi-ring heterocycle, either of which may be optionally substituted. In some embodiments, the term "multi-ring" refers to a compound having 3-5 fused ring structures (such as anthracene, naphthofuran, perylene or pyrene). Conjugation of electrons in these aromatic systems may result in a low energy π* lowest unoccupied molecular orbital and a low energy delocalized excited state. Thus, such conjugated compounds are electron donors and may be used for redox sensing of electron-deficient analytes, such as nitrogen-based explosives, through electron-transfer luminescence quenching. In some embodiments, the small molecule fluorophore is an aromatic four-ring hydrocarbon or an aromatic four-ring heterocycle, which may be optionally substituted. In some embodiments, the aromatic multi-ring hydrocarbon or the aromatic multi-ring heterocycle is substituted with an electron donating group. Electron donating groups are known to those of skill in the art.

In some embodiments, the polyamine polymer functionalized with a small molecule fluorophore comprises a plurality of structural units corresponding to Formula (I):

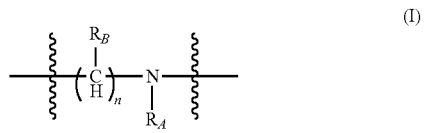

wherein each $R_A$ is selected independently from the group consisting of hydrogen, Formula (II) and Formula (III):

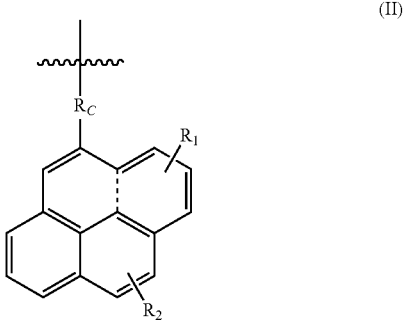

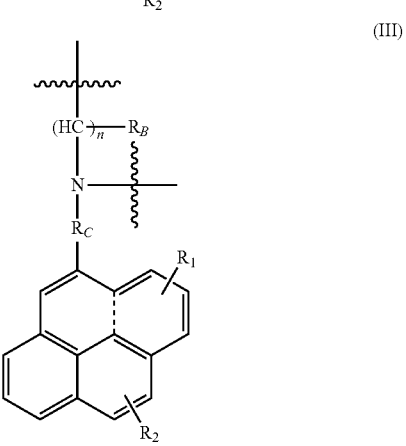

wherein each $R_C$ is selected independently from the group consisting of hydrogen and —C(O)—$C_{2-6}$ alkyl-;

wherein $R_1$ and $R_2$ are each independently selected from hydrogen, cyano, $C_{1-4}$ alkyl, —B(OH)$_2$, —C(O)H, —$C_{1-4}$ alkyl-C(O)H, —C(O)CH$_3$, —$C_{1-4}$ alkyl-C(O)CH$_3$, —C(O)OH, —$C_{1-4}$ alkyl-C(O)OH, —C(O)OCH$_3$, —$C_{1-4}$ alkyl-C(O)OCH$_3$ and —$C_{1-4}$ alkyl-C(O)O-succinimide;

$R_B$ is selected from the group consisting of a bond, hydrogen, amine and $C_1$-$C_3$ alkyl; and each n is selected independently from 2-8.

It is to be understood that the symbol "⸹" denotes the position of attachment of the structural units to other structural units. The other structural units may be other monomer units or terminal groups, such as hydrogens.

Preferably, $R_C$ is an hydrogen or —C(O)—$C_{2-4}$ alkyl-, more preferably a hydrogen or —C(O)—$C_{3-4}$ alkyl-, and even more preferably a hydrogen or —C(O)—$C_3$ alkyl-.

Preferably, $R_B$ is selected from the group consisting of a bond and hydrogen; and more preferably hydrogen.

Each n is selected independently from 2-8. The polyamine polymer may include a copolymer or block copolymer comprising one or more monomers. Preferably, n is selected independently from 2-6, and more preferably, n is 2, 3 or 6.

The small molecule fluorophore may be selected from the group consisting of pyrene, 1-pyrenebutyric acid, pyrene-1- boronic acid, 1-pyrenebutyric acid N-hydroxysuccinimide ester, 5-carboxy-2,7-dichlorofluorescein; 5-Carboxyfluorescein (5-FAM); 5(6)-carboxyfluorescein-N-hydroxysuccinimide ester (C1609); 5-HAT (Hydroxy Tryptamine); 5-Hydroxy Tryptamine (HAT); 6-Carboxyrhodamine 6G; 6-CR 6G; 6-JOE; Acridine Orange+DNA; Acriflavin; Alexa Fluor 430™; Alexa Fluor 488™; Alexa Fluor 500™; APTRA-BTC=Ratio Dye, $Zn^{2+}$; bis-BTC=Ratio Dye, $Zn^{2+}$; APTS; AmCyan; Astrazon Orange R; Aurophosphine; BCECF (high pH); Beta Lactamase; Bodipy 492/515; Bodipy 500/510; Bodipy F1; Bodipy FL ATP; Bodipy F1-Ceramide; Brilliant Sulphoflavin FF; BTC—Ratio Dye $Ca^{2+}$; BTC-5N—atio Dye, $Zn^{2+}$; Calcein; Calcium Green; Calcium Green-I $Ca^{2+}$ Dye; Calcium Green-2 $Ca^{2+}$; Calcium Green-5N $Ca^{2+}$; Calcium Green-C18 $Ca^{2+}$; CFDA; CFSE; CL-NERF (Ratio Dye, pH); CMFDA; cyclic AMP Fluorosensor (FiCRhR); CyQuant Cell Proliferation Assay; Dansyl Amine; Dansyl Cadaverine; Dansyl Chloride; Dansyl DHPE; DCFDA; DCFH (Dichlorodihydrofluorescein Diacetate); DHR (Dihydorhodamine 123); Dichlorodihydrofluorescein Diacetate (DCFH); Dihydrohodamine 123 (DHR); DiO (DiOC (3)); DM-NERF (high pH); Dopamine; DTAF; DyeCycle™ Green; DyeCycle™; Orange; EGFP; ELF 97; Eosin; Euchrysin; EYFP; FDA; FITC; FITC Antibody; Fluo-3; Fluo-4; Fluorescein-EX; Fluorescein Diacetate; Fluoro-Emerald; Fluoro-Gold (Hydroxystilbamidine); FluorX; Fura-2, high calcium; Fura-2, low calcium; GFP (S65T); GFP red shifted (rsGFP); GFP wild type, non-UV excitation (wtGFP); GFP wild type, UV excitation (wtGFP); GFPuv; Hydroxystilbamidine (FluoroGold); Hydroxytryptamine; JC-1; JO-JO-1; JO-PRO-1; LIVE/DEAD Kit Animal Cells; Lucifer Yellow; Lyso Tracker Blue-White; Lyso Tracker Green; Lyso Tracker Red; LysoSensor Green; LysoSensor Yellow/Blue; Mag Green; Mag-Fura-2; Mag-Fura-5; Magnesium Green; Monobromobimane (mBBr-GSH); NBD; NBD Amine; Nitrobenzoxadiazole; Noradrenaline; Nylosan Brilliant Iavin E8G; Oregon Green; Oregon Green 488-X; Oregon Green™ 503; Oregon Green™ 488; Oregon Green™ 500; Oregon Green™ 514; pHrodo™ dye; PKH67; Primuline; Pyronine; Qdot 525 nanocrystal; Quinacrine Mustard; Rhodamine 110; Rhodamine 123; Rhodamine Green; rsGFP; S65A; S65C; S65L; S65T; Sapphire GFP; Serotonin; Sevron Orange; sgGFP™ (super glow GFP); Sodium Green; SpectrumGreen; SYTO 11; SYTO 12; SYTO 13; SYTO 14; SYTO 15; SYTO 16; SYTO 20; SYTO 21; SYTO 22; SYTO 23; SYTO 24; SYTO 80; SYTO 81; SYTOX Green; Tetracycline; Thiazole Orange; Thioflavin 5; Thioflavin S; TO-PRO-1; TOTO-1; Uranine B; wt GFP; Y66F; Yellow GFP; YFP; YO-PRO-1 and YOYO-1, and mixtures thereof. Preferably, the small molecule fluorophore is selected from the group consisting of pyrene, 1-pyrenebutyric acid, pyrene-1-boronic acid, 1-pyrenebutyric acid N-hydroxysuccinimide ester, and mixtures thereof. The fluorophore selected may be chemically attached or covalently bound to the polyamine polymer by any chemistry known to one skilled in the art. The fluorophore to be bound may first be chemically modified to comprise a linking group and/or linking moiety capable of being chemically attached or covalently bound to the polyamine polymer (e.g. the $R_C$ group).

In one embodiment, the polyamine polymer functionalized with a small molecule fluorophore is a branched polyethylenimine functionalized with 1-pyrenebutyric acid.

In some embodiments, properties of the compounds may be tuned using particular substituents in order to produce a desired emission wavelength. Those skilled in the art would recognize which types of functional groups would afford this tuning ability. For example, electron-poor groups, such as acyl, carboxyl, cyano, nitro, sulfonate, or the like, may provide fluorescence emission at shorter wavelengths, whereas electron-rich groups, such as amino, hydroxy, alkoxy (e.g. methoxy), acylamino, acyloxy, alkyl, halide, and the like, may provide fluorescence emission at longer wavelengths.

In some embodiments, the small molecule fluorophore is substantially evenly distributed throughout the polymer. Even distribution may be advantageous, for example, in providing highly uniform fluorescence throughout the polymer. However, it is to be understood that even distribution is not necessary for proper function of the highly sensitive explosives detection polymers described herein. As used herein, the phrase "substantially evenly distributed" refers to a distribution of particles such that the amount of particles differs less than about 5% between any two distinct portions of the polymer. In some embodiments, the amount of fluorophore particles differs less than about 4% between any two distinct portions of the polymer. In some embodiments, the amount of fluorophore particles differs less than about 3% between any two distinct portions of the polymer. In some embodiments, the amount of fluorophore particles differs less than about 2%, less than about 1%, less than about 0.5%, or even less than about 0.1% between any two distinct portions of the polymer.

In some embodiments, the small molecule fluorophore (e.g. the pyrene-based molecule) is present in the polyamine polymer at about 1% to about 60%, by molar ratio of pyrene to primary amine. It is to be understood that too much or too little fluorophore may, depending upon the fluorophore itself, change the amount and nature of charge transfer band and π-π interactions, among other interactions described herein, and thus potentially the sensitivity of the polymer. Accordingly, in some embodiments, the small molecule fluorophore is present in the polyamine polymer at about 2% to about 55%, by molar ratio of pyrene to primary amine. In some embodiments, the small molecule fluorophore is present in the polyamine polymer at about 5% to about 45%, by molar ratio of pyrene to primary amine. In some embodiments, the small molecule fluorophore is present in the polyamine polymer at about 10% to about 35%, by molar ratio of pyrene to primary amine. In some embodiments, the small molecule fluorophore is present in the polyamine polymer at about 15% to about 25%, by molar ratio of pyrene to primary amine. In some embodiments, the small molecule fluorophore is present in the polyamine polymer at about 20% by molar ratio of pyrene to primary amine.

In some embodiments, the present disclosure provides polymers that function in aqueous environments. In an aqueous environment, the polymer may swell/de-swell, similar to a hydrogel. As a result of this swelling behavior, as well as the nature of the polyamine polymer and other factors, the polymer may be porous. As used herein, "porous" refers to a porosity of at least about 10%. The term porosity is used to denote the ratio of the volume of all the pores (e.g. open spaces) in the material to the volume of the whole thereof. Accordingly, the ratio of the open spaces is specified in percent (%) with respect to the external volume, which would correspond to 100%. In some embodiments, the porosity of the polymer is in a range of between about 5% and about 90%, for example between about 10% and about 80%. In some embodiments, the porosity of the polymer is in a range of between about 20% and about 65%. In some embodiments, the porosity of the polymer is in a range of between about 20% and about 55%. In some embodiments, the porosity of the polymer is in a range of between about 20% and about 45%. In some embodiments, the porosity of the polymer is in a range of between about 20% and about 35%. In some embodiments, the porosity of the polymer is in a range of between about 30% and about 65%. In some embodiments, the porosity of the polymer is in a range of between about 30% and about 55%. In some embodiments, the porosity of the polymer is in a range of between about 30% and about 45%. Without wishing to be bound by any particular theory, it is believed that a high porosity may be advantageous in allowing the analyte to permeate the material and maximize contact with the fluorophore. It is to be understood, however, that a material with low porosity and/or low surface area (e.g., films) will also allow proper function of the explosives detection polymers described herein.

In some embodiments, the present disclosure provides a highly sensitive polymer material. Accordingly, in some embodiments, the polymer is capable of detecting an explosive material in very small amounts. In some embodiments, the polymer is capable of detecting the presence of explosive material at concentrations as low as about 200 ppb. In some embodiments, the polymer is capable of detecting the presence of explosive material at concentrations as low as about 150 ppb. In some embodiments, the polymer is capable of detecting the presence of explosive material at concentrations as low as about 100 ppb, as low as about 75 ppb, as low as about 50 ppb, as low as about 25 ppb, as low as about 10 ppb, as low as about 5 ppb, as low as about 1 ppb, as low as about 0.5 ppb, as low as about 0.1 ppb, as low as about 0.01 ppb, or even as low as about 0.001 ppb. In some embodiments, the polymer is capable of detecting the presence of explosive material at concentrations as low as about 1 ppt, as low as about 0.5 ppb, as low as about 0.1 ppt, or even as low as about 0.01 ppt. In some embodiments, explosive material at concentrations as low as about 25 ppb can be visualized by the naked eye. In some embodiments, explosive material at concentrations as low as about 10 ppb can be visualized by the naked eye. In some embodiments, explosive material at concentrations as low as about 5 ppb can be visualized by the naked eye.

In some cases, sensitivity is measured by the amount (in weight) of explosive material required to produce fluorescence quenching. In some embodiments, the polymer is capable of producing fluorescence quenching (e.g. directly visible fluorescence quenching) in the presence of an explosive material in an amount less than about 1 µg, less than about 500 ng, less than about 250 ng, less than about 100 ng, less than about 50 ng, or less than about 25 ng. In some embodiments, the polymer is capable of producing fluorescence quenching in the presence of an explosive material in an amount less than about 10 ng. In some embodiments, the polymer is capable of producing fluorescence quenching in the presence of an explosive material in an amount less than about 5 ng. In some embodiments, the polymer is capable of producing fluorescence quenching in the presence of an explosive material in an amount less than about 1 ng, less than about 0.1 ng or less than about 0.01 ng.

In some embodiments, the present disclosure provides a polymer material that allows for quick detection of explosive materials. In some embodiments, for example, the polymer is capable of detecting an explosive material in less than about 6 minutes. In some embodiments the polymer is capable of detecting an explosive material in less than about 5 minutes. In some embodiments the polymer is capable of detecting an explosive material in less than about 4 minutes. In some embodiments the polymer is capable of detecting an explosive material in less than about 3 minutes, less than about 2 minutes, less than about 1 minute, less than about 30 seconds, less than about 20 seconds, or less than about 10 seconds. In some embodiments the polymer is capable of detecting an explosive material in less than about 5 seconds. The time of detection can vary within the parameters above, but will generally depend upon the concentration of explosive material exposed to the polymer.

Methods for Explosives Detection

The present disclosure provides methods for detecting an explosive material. The method includes, for example, contacting the explosives detecting polymer as described herein with an explosive material for a given period of time; measuring the amount of fluorescence emitted by the explosives detecting polymer; and comparing the amount of fluorescence with a suitable control. In such methods, an explosive material is detected where the fluorescence of the explosives detecting polymer is less than the fluorescence of the suitable control. In other embodiments, the present disclosure provides methods for screening a test sample for the presence of an explosive material. The method includes, for example, contacting the explosives detecting polymer as described herein with the test sample for a given period of time; measuring the amount of fluorescence emitted by the explosives detecting polymer; and comparing the amount of fluorescence with a suitable control. In such methods, the presence of an explosive material is detected in the test sample where the fluorescence of the explosives detecting polymer is less than the fluorescence of the suitable control.

In some embodiments, the present disclosure utilizes luminescent compounds to detect explosive materials (e.g. nitrogen-based explosives) through luminescence quenching. Direct interaction of an electron-accepting analyte (such as an explosive material) with a small molecule fluorophore in the explosives detecting polymer described herein can cause luminescence quenching. Such quenching can be monitored to identify the presence of explosives. For example, a polymer may be exposed to an environment suspected of being contaminated with explosives and subsequently observed to determine the presence of explosives through luminescence quenching.

The polymers may be designed to employ a dual and sequential quenching mechanisms (i.e. latent Förster resonance energy transfer (FRET) followed by photoinduced electron transfer (PET)). In PET process (FIG. 1a), the energy gap between the lowest unoccupied molecular orbital (LUMO) of donor fluorophore and that of the acceptor NACs is approximately the thermodynamic driving force for the oxidative electron transfer process. In FRET process (FIG. 1b), an initially excited molecule (donor) returns to the ground state orbital, while simultaneously the transferred energy promotes an electron on the acceptor to the excited state. If donor emission energies are sufficiently coincident with acceptor absorption energies, such coupling can permit the resonance transitions to take place. If the donor is a fluorophore but the acceptor is non-emissive, a 'fluorescence-quenching' may be observed in a FRET process. For example, when the donor-acceptor distance is less than about 10 nm, the FRET may be a dominant process in a fluorescence quenching. The dipole-dipole interaction in FRET could be measured up to a range of about 80-100 Å in a favorable case, while in photo-induced electron transfer (PET), as a comparison, can only occur within a few Å.

The present disclosure also provides methods comprises the steps of contacting the explosives detecting polymer with an explosive material for a given period of time, wherein the polymer comprises polyamine polymer functionalized with a small fluoropolymer having a defined fluorescence emission energy band, the explosive material having defined absorbance energy band, wherein the fluorescence emission energy band and the absorbance energy band are sufficiently coincident to allow coupling. Preferably, the fluorescence emission energy band and the absorbance energy band are less than about 50 nm apart, more preferably less than about 10 nm, and even more preferably less than about 5 nm.

In some embodiments, the explosives detecting polymer is contacted with an explosive material (or a test sample) for at least about 6 minutes. In some embodiments, the explosives detecting polymer is contacted with an explosive material (or a test sample) for at least about 30 seconds. In some embodiments, the explosives detecting polymer is contacted with an explosive material for at least about 1 seconds. In some embodiments, the explosives detecting polymer is contacted with an explosive material for at least about 5 minutes, at least about 4 minutes, at least about 3 minutes, at least about 2 minutes, at least about 1 minute, at least about 45 seconds, or at least about 15 seconds. In some embodiments, the explosives detecting polymer is contacted with an explosive material (or a test sample) for less than about 6 minutes, less than about 5 minutes, less than about 4 minutes, less than about 3 minutes, less than about 2 minutes, less than about 1.5 minutes, less than about 60 seconds, less than about 30 seconds, less than about 15 seconds, less than about 10 seconds, or even less than about 5 seconds. In some embodiments, the explosives detecting polymer is contacted with an explosive material (or a test sample) for a time period of between about 1 second and about 6 minutes. The time of exposure will depend upon the concentration of explosive material in the sample (or suspected to be in the sample). For example, a sample may be exposed to the polymer for a longer period of time, but begin to show quenching after only a few seconds. In some embodiments, the explosives detecting polymer is contacted with an explosive material (or a test sample) for about six minutes or until quenching occurs, whichever is greater.

As used herein, the term "suitable control" refers to a control based upon fluorescence levels in an explosives detection polymer that has not been exposed to an explosive material. That is, in some embodiments, the suitable control is a predetermined fluorescence level or value. In some embodiments, the suitable control is a fluorescence level detected from a single explosives detection polymer known to have not been exposed to an explosive material. In some embodiments, the suitable control is an average fluorescence level from a plurality of explosives detection polymers which have not been exposed to an explosive material. In some embodiments, the suitable control is a fluorescence level detected in a portion of the explosives detection polymer that has not been exposed to an explosive material. For example, often detection of an explosive material may be confirmed by visually observing (e.g. under UV light) dark quenched spots amidst the bright background of the explosives detection polymer. In this situation, the bright background would be the suitable control.

In some embodiments, the present disclosure provides an explosives detection polymer capable of simultaneously detecting a wide range of explosive materials, such as nitrogen-based explosives, including nitroaromatic-, nitramine- and organic nitrate-based explosives. Many nitrogen-based explosives are electron-acceptors. In nitroaromatics, for example, the π* lowest unoccupied molecular orbitals (LUMOs) are of low energy due to the electron-withdrawing effect of the nitro substituent on the aromatic ring. A higher degree of nitro-substitution results in a higher reduction potential and a greater oxidizing ability (nitrobenzene (−1.15 V), dinitrotoluene (−0.9 V), and trinitrotoluene (−0.7 V), versus normal hydrogen electrode (NHE)). Similarly, organic molecules functionalized with nitro groups have lower energy LUMOs, which increase their oxidizing abilities. Thus, organic nitro compounds, such as the nitramine explosives (e.g. RDX) and the organic nitrates (e.g. PETN and nitroglycerin), have increased electron-accepting abilities compared to certain other organic compounds.

In some embodiments, the methods of the present disclosure are capable of detecting an explosive listed in Bureau of Alcohol, Tobacco and Firearms *Commerce in Explosives; List of Explosive Materials* (2010R-27T), Federal Register, Vol. 75, No. 221, P 70291, 2010. In some embodiments, the present disclosure provides an explosives detection polymer capable of detecting explosive materials, including, but are not limited to octahydro-1,3,5,7-tetranitro-1,3,5,7-tetrazocine (HMX), hexahydro-1,3,5-trinitro-1,3,5-triazine (RDX), 1,3,5-trinitrobenzene (TNB), 1,3-dinitrobenzene (DNB), methyl-2,4,6-trinitrophenylnitramine (Tetryl), nitrobenzene (NB), 2,4,6-trinitrotoluene (TNT), picric acid (PA), ammonium perchlorate (AP), 2,4-dinitrotoluene (24DNT), 2,6-dinitrotoluene (26DNT), o-nitrotoluene (2NT), m-nitrotoluene (3NT), p-nitrotoluene (4NT), nitroglycerin (NG), 4-amino-2,6-dinitrotoluene (4-Am-DNT), 2-amino-4,6-dinitrotoluene (2-Am-DNT), pentaerythritol tetranitrate (PETN), 2,3-dimethyl-2,3-dinitrobutane (DMNB), hexanitrostilbene (HNS), nitroamines, nitroamides, nitroesters, other nitro- or nitrate-containing species, and the like. Explosive molecules have various degrees of solubility, mostly low, and the presence of the above compounds can indicate the presence of explosives in a sample. In some embodiments, the present disclosure provides methods of detecting Tetryl, TNT, TNB, DNT, DNB and/or NB in a sample suspected of containing an explosive material.

In some embodiments, the methods of the present disclosure detect an explosive material in very small amounts. In some embodiments, the methods of the present disclosure detect the presence of explosive material at concentrations as low as about 200 ppb, as low as about 150 ppb, as low as about 100 ppb, as low as about 90 ppb, as low as about 80 ppb, as low as about 70 ppb, as low as about 60 ppb, as low as about 50 ppb, as low as about 40 ppb, as low as about 30 ppb, as low as about 20 ppb, as low as about 10 ppb, as low as about 5 ppb, as low as about 1 ppb, as low as about 0.5 ppb, as low as about 0.1 ppb, as low as about 0.01 ppb, or even as low as about 0.001 ppb. In some embodiments, the methods of the present disclosure detect the presence of explosive material at concentrations as low as about 1 ppt, as low as about 0.5 ppb, as low as about 0.1 ppt, or even as low as about 0.01 ppt. In some embodiments, explosive material at concentrations as low as about 25 ppb can be visualized by the naked eye. In some embodiments, fluorescence quenching resulting from the presence of explosive material at concentrations as low as about 10 ppb can be visualized by the naked eye (e.g. when material is illuminated with UV light). In some embodiments, fluorescence quenching resulting from the presence of explosive material at concentrations as low as about 5 ppb can be visualized by the naked eye (e.g. when material is illuminated with UV light). In some embodiments, the methods of the present disclosure are capable of detecting an explosive material in an amount less than about 10 ng. In some embodiments, the methods of the present disclosure are capable of detecting an explosive material in an amount less than about 1 ng.

In some embodiments (e.g. if the fluorophore is luminescent in the visible spectrum) the quenching may be observed through either direct or indirect visual examination. In some embodiments, the polymer is placed in a dark environment and exposed to a wavelength of light capable of exciting luminescence from the reagent. The excitation source utilized may be, for example, a black light, a blue light, a white light, a UV lamp, a mercury-deuterium lamp, xenon-arc lamp, light emitting diodes, or cathode ray tubes. The excitation source or light source can be chosen to maximize excitation of the luminescent compound while simultaneously minimizing the degree of photodegradation. In some embodiments, quenching may be observed through indirect visual examination using a camera or other instrumentation as an intermediary. Additionally or alternatively, the quenching may be recorded with the use of a visible or ultra-violet camera, or with the use of a fluorimeter or fluorescence spectrometer. The instrumentally recorded data may be analyzed directly or by using computer software to interpret results and make a determination of whether or not explosives are present.

In some embodiments, the quenching may be observed as a change in the emission of the explosives detection polymer, for example a change in the wavelength of the luminescence emission. Accordingly, in some embodiments, methods of the invention can include determining a change in the wavelength of the luminescence emission. Methods for determining changes in wavelength are known in the art.

In some embodiments, the method is performed at an elevated temperature to increase the interaction of the explosive material and the polymer. Preferable, the method is performed at temperature ranging from about 0° C. to about 100° C.

In some embodiments, the method is performed at a certain pH, or pH range, to effect explosive solubility and polymer swelling. Preferable, the method is performed at a pH ranging from about 5 to about 14.

The methods of the present invention allow for the detection of explosive materials in an aqueous environment. The aqueous environment may be an aqueous sample generated from explosive in water, in the air and on surfaces such as groundwater, seawater, liquid containers, hands, clothing, cars, packages, luggage, door handles, buildings, land, desks, computers, and more.

Methods for Forming Polymers

The present disclosure provides methods for forming an explosives detecting polymer. The method includes any synthesis route known in the art that may be employed to functionalize a polyamine polymer with a pyrene-based fluorophore.

In some embodiments, the method involves aminolysis of a small molecular fluorophore having a leaving group, such as N-hydroxysuccinimide ester, with the amine groups in a polyamine polymer. The method for forming a polyamine functionalized with a small molecule fluorophore may comprise providing a polyamine polymer having a structure corresponding to Formula (I):

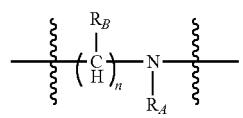

wherein each $R_A$ is selected independently from the group consisting of hydrogen and a repeating structure corresponding to Formula (I);

$R_B$ is selected from the group consisting of a bond, hydrogen, amine and $C_1$-$C_3$ alkyl; and each n is selected independently from 2-8; and reacting the polyamine polymer with an ester having a structure corresponding to Formula (IV):

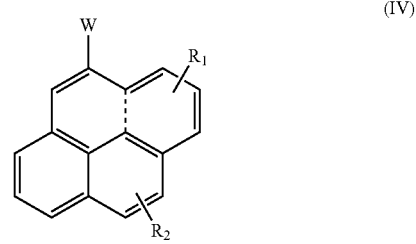

wherein W is —$C_{2-6}$ alkyl-C(O)-LG,
wherein LG is a leaving group,
wherein $R_1$ and $R_2$ are each independently selected from hydrogen, cyano, $C_{1-4}$ alkyl, —B(OH)$_2$, —C(O)H, —$C_{1-4}$ alkyl-C(O)H, —C(O)CH$_3$, —$C_{1-4}$ alkyl-C(O)CH$_3$, —C(O)OH, —$C_{1-4}$ alkyl-C(O)OH, —C(O)OCH$_3$, —$C_{1-4}$ alkyl-C(O)OCH$_3$ and —$C_{1-4}$ alkyl-C(O)O-succinimide;
wherein the polyamine polymer functionalized with a small molecule fluorophore is formed.

The leaving group may be selected from any leaving or protecting group known in the art, including succinimide based groups, such as N-hydroxysuccinimide ester.

The polyamine polymer functionalized with a small molecule fluorophore may have an excess amount of amine groups in relation to the small molecule fluorophore. An excess of amine groups may be beneficial to form a polyamine polymer with evenly distributed small molecule fluorophores, as well as allow for sufficient amine groups for analytes, such as NACs, to form amine complexes that are located near, or close to, the small molecule fluorophore. Preferably, the ratio of amine groups in the polyamine polymer to small molecule fluorophore is greater than 2:1, preferably the ratio is greater than 7:1, more preferably the ratio is greater than 10:1.

Sensors and/or Kits for Explosive Detection

The present disclosure provides sensors and/or kits for explosives detection. In some embodiments, the sensors and/or kits include the explosives detecting polymer described hereinabove. A "sensor" refers to any device or article capable of detecting an explosive material.

In some embodiments, the kits include a polyamine polymer and a small molecule fluorophore, packaged with instructions for forming an explosives detecting polymer. In some embodiments, the kit further includes a UV light (e.g. a handheld UV light) and/or instructions for detecting an explosive material. In some embodiments, the kit includes the sensing polymer printed on test paper.

The sensor may further comprise other common features of explosives detectors, for example, an emission detector positioned to detect fluorescence emission (or lack thereof); an inlet for intake of a sample (e.g. solution sample); and/or a sample cell constructed and arranged to receive the sample. In some embodiments, the sensor includes a complementary analytical device (e.g. a device which performs fluorimetry, absorption spectroscopy, mass spectroscopy, Raman) and/or other appropriate analytical technique. Such analytical devices, when utilized with the explosives detection polymers of the present disclosure, can increase the sensitivity of a sensor. In some embodiments, the sensor includes a fluorimeter. The use of a fluorimeter in conjunction with the explosives detection polymer of the present disclosure may increase the sensitivity of a sensor by allowing the detection of very small changes is fluorescence intensity (e.g. changes that may not be noticeable upon direct visual inspection). The use of a fluorimeter in conjunction with the explosives detection polymer of the present disclosure may also decrease the time required to detect the presence of an explosive material. For example, it may take a few minutes to visually inspect a polymer for quenching, whereas the use of a sensor (e.g. with a fluorimeter) may only require a few seconds. In some embodiments, the sensor includes an absorption spectrometer. In some embodiments, the sensor includes a mass spectrometer.

In one embodiment, the sensor also includes an article to provide enhanced rigidity, sensitivity, selectivity, stability, or a combination of any number of these features, to the explosives detection polymer in the sensor. The article can be positioned adjacent the polymer and can be selected from beads, nanoparticles, polymer fibers, waveguides and a film. In one embodiment, a sensor can be provided comprising an explosives detection polymer positioned adjacent to a waveguide. Light emitted by the explosives detection polymer in one area can be captured by internal reflection in the polymer and then reabsorbed and re-emitted in a different region of the sensor. This process can occur many times before reaching a detector, resulting in a sensor with enhanced sensitivity. Sequential emission and reabsorption cycles increase the probability that an excitation will be quenched or trapped by an analyte.

In some embodiments, the kit and/or sensor is a robot or a remote controlled device. For example, in some embodiments, the explosives detection polymer can be incorporated into a remote controlled vehicle, such as an unmanned vehicle. Placing the explosives detection polymer into a non-human system can result in fast screening of test environments in large scale with little or no danger to humans.

EXEMPLIFICATION

The methods of this invention can be understood further by the following examples. It will be appreciated, however, that these examples do not limit the invention. Variations of the invention, now known or further developed, are considered to fall within the scope of the present invention as described herein and as hereinafter claimed.

Example 1

Preparation and Characterization of 1-pyrenebutyric acid-polyethylenimine

An exemplary explosive detection polymer was fabricated by aminolysis of 1-pyrenebutyric acid N-hydroxysuccinimide ester with the primary amine groups in branched PEI. The one-step aminolysis reaction is facile and cost-effective. Briefly, 0.154 g of 1-pyrenebutyric acid N-hydroxysuccinimide ester (PBANHSE) was dissolved in 6 mL N,N-dimethylformamide (DMF) and then mixed with 2.12 g branched PEI (Mw=750,000 Da, Mn=60,000 Da, Supelco), followed by gently stirring at room temperature for 24 h to allow the conjugation to proceed. The formed brown solution was slowly poured into ethyl ether, and the resulting yellow precipitate was extensively washed with THF and $H_2O$ to remove reactant residues. After drying under vacuum for 24 h at room temperature, the final polymer product shows a light yellow colour.

Due to its poor solubility, 1-pyrenebutyric acid-PEI (generally, "pyrene-PEI") was sonicated and suspended in DI $H_2O$ for NACs detection. Briefly, 100 mg as-prepared pyrene-PEI was dispersed in 100 mL DI $H_2O$ by a cup—horn sonicator (Cole—Parmer Ultrasonic Processor, 750 W, 100% amplitude) for 30 min in an ice—water bath, followed by centrifuged at 7,200 rpm for 30 min to remove any large particles. The upper 80% supernatant was carefully decanted to ensure well-dispersed pyrene-PEI suspension, and then stored at room temperature for future use.

General sensing experiments for NAC explosives were carried out by monitoring the fluorescence quenching behavior of pyrene-PEI upon the addition of target NACs at room temperature. Briefly, 3 mL of pyrene-PEI suspension was placed in a disposal methacrylate cuvette with 1 cm width and then explosives solution was added successively. Each titration was repeated at least three times to ensure good reproducibility. The fluorescence emission data were collected in the wavelength region of 360-600 nm with an excitation wavelength of 343 nm. The fluorescence quenching efficiency was defined as $(I_0-I)/I_0 \times 100\%$, where $I_0$ and I are peak intensities before and after the addition of analytes. Similar procedure was applied to investigate the interferences such as toluene, benzaldehyde, benzonitrile, phenol, and aniline. (See Selectivity Example).

Absorption spectra were performed on a Cary 50 UV-vis spectrophotometer (Agilent Technologies), and fluorescence emission spectra were recorded on a Varian Cary Eclipse fluorescence spectrophotometer (Agilent Technologies).

Figure 2:
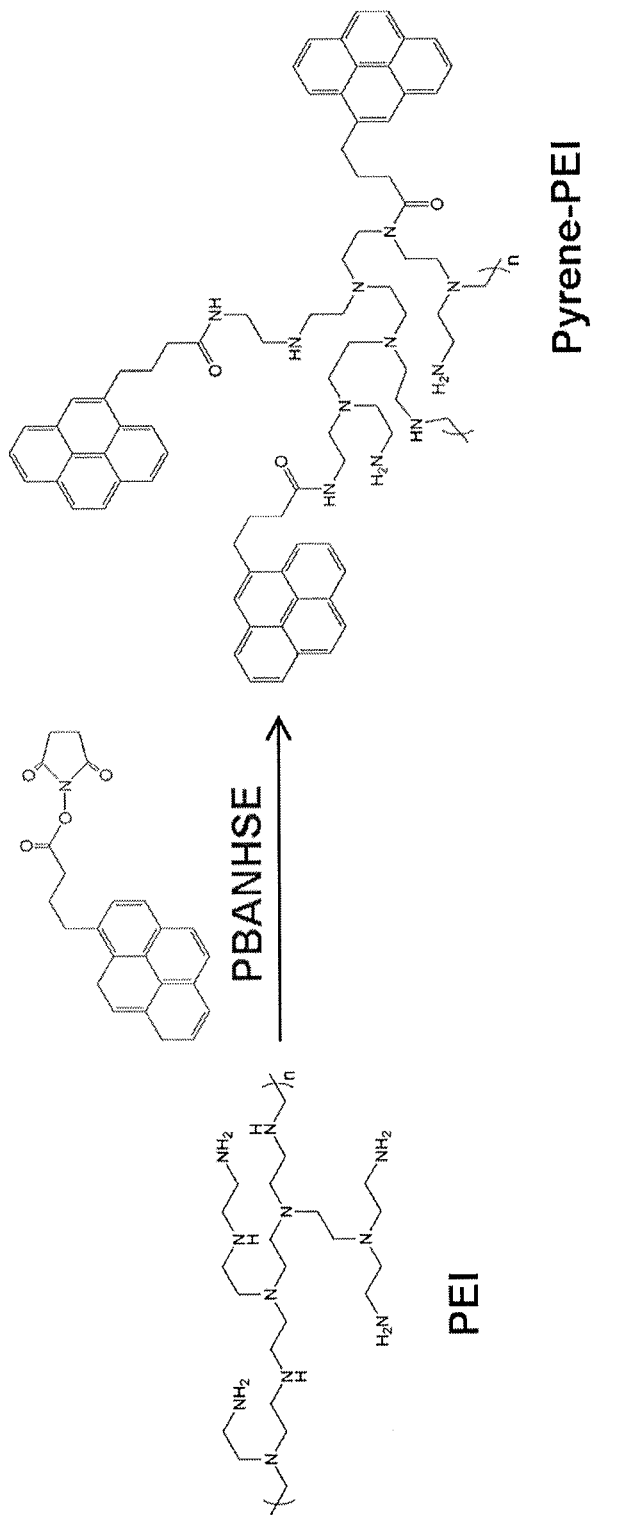
FIG. 2 shows one embodiment of the present disclosure wherein a polyamine polymer (PEI) is reacted with a protected small molecule fluorophore (PBANHSE) to form a polyamine polymer functionalized with a small molecule fluorophore (Pyrene-PEI).
Figure 3:
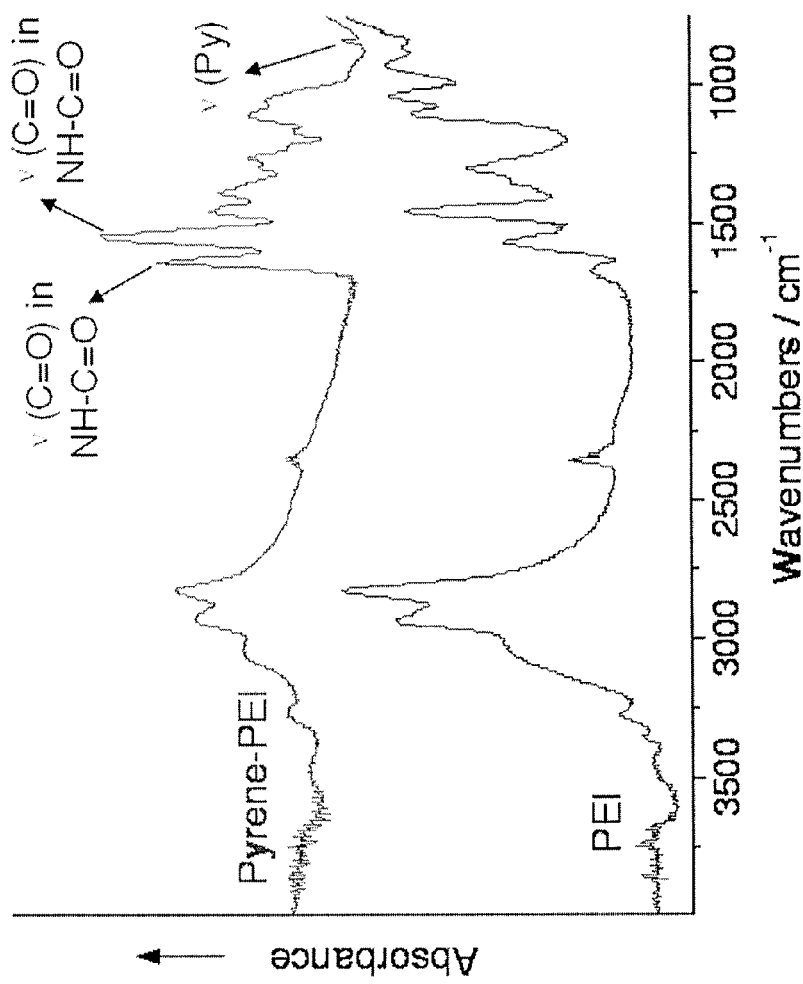
FIG. 3 shows the FT-IR spectrum for the PEI and Pyrene-PEI as described in the Examples.

In this example, PBANHSE was chosen because pyrene butyric acid (PBA) is sensitive to NACs and its NHS ester allows efficient nucleophilic reaction with the primary and secondary amines of PEI to create stable amide bonds, as shown in FIG. 2. The conjugation reaction proceeded smoothly and generated the desirable product with a high yield, as characterized by FT-IR (FIG. 3), from which the peaks corresponding to pyrene and NH—CO bond were revealed, indicating the successful conjugation of pyrene with PEI. In FIG. 3, the attenuated total reflectance Fourier transform infrared (ATR-FTIR) spectra were collected using a ZnSe internal reflection element (IRE) obtained on a Nicolet Magna-IR 560 spectrophotometer (Brucker, Germany). The IR spectra were analyzed using the software of Omnic 7.2a from Thermo Electron Corporation. The successful functionalization of PEI with pyrenyl units was further demonstrated spectroscopically. As shown in the FT-IR spectra in FIG. 3, three new adsorption peaks at 843 $cm^{-1}$ (corresponding to vPyrene), 1640 $cm^{-1}$ and 1550 $cm^{-1}$ (both corresponding to the vC=O in NH—C=O) were observed for pyrene-PEI polymer, indicating the presence of pyrene and the successful linkage between the carbonyl groups from PBANHSE and the amine groups from PEI.

Figure 4:
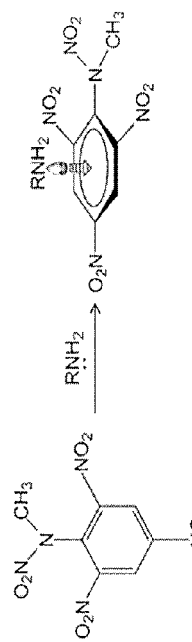
FIG. 4 shows in the interaction between Tetryl and primary amines through the charge-transfer mechanism to form a Meisenheimer complex (FIG. 4a), and the adsorption (black) and emission (red) spectra of pyrene-PEI (dot line) and a Tetryl/pyrene-PEI (solid line) solution (FIG. 4b). The vial inserts show optical images of pyrene-PEI (left) and Tetryl/pyrene-PEI (right) under white light (top) and 275-nm UV lamp (bottom).
Figure 4:
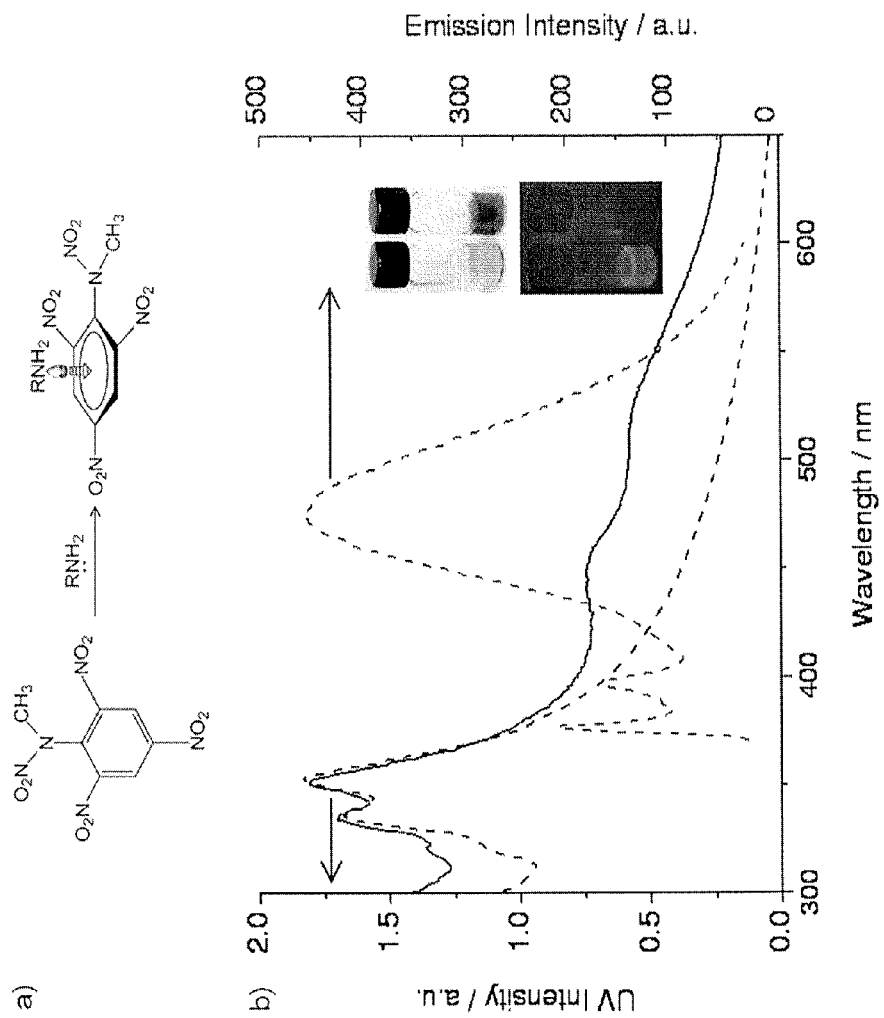
Figure 5:
FIG. 5 shows one embodiment of the present disclosure wherein polyamine polymers functionalized with small molecule fluorophores (Pyrene-PEI) form a hyperlinked structure through π-π stacking of pyrene on the polymer branches.

Since PEI is colourless and non-emissive in solution, the photoluminescence property of the pyrene-PEI polymer is majorly attributed to the covalently-linked pyrenyl units. The UV-vis absorption and photoluminescence spectra were collected in the ultrasonicated pyrene-PEI suspension and presented in FIG. 4. The absorption spectrum exhibits two prominent peaks at 326 and 343 nm, corresponding to the singlet vibrational bands (S0→S2) of pyrenyl units. The fluorescence emission of pyrene-PEI was similar to that of pure pyrene solution, which consists of two bands: The first band including several peaks is in the near UV region (ca. 370 to 410 nm) and consistent with the emission from singlet excited pyrene (monomer), while the second band consists of a dominant broad peak centered at 470 nm and could be ascribed to pyrene excited dimmers or "excimers" through the π-π stacking of pyrene monomers. Co-facial π-π stacking of pyrenyl units may be formed among pyrenes anchored on PEI, thus generating a shape-persistent and three-dimensional hyperlinked network, as depicted in FIG. 5. FIG. 5 shows a hyperlinked structure of pyrene-PEI through π-π stacking of pyrene on polymer branches. This proposed hyperlinked network for pyrene-PEI may also be implied by its solubility study, which shows that pyrene-PEI is insoluble in most common organic/inorganic solvents, including DI $H_2O$, ethanol, THF, DMF, hexane, toluene and dichloromethane. However, it possesses a fair degree of swellability in polar solvents, such as water and ethanol, probably due to the polar nature of the as-prepared pyrene-PEI and its three-dimensional networks could be relaxed or swelled when its excessive amines are exposed to polar solvents, a similar property as 'hydrogel'. Without wishing to be bound by any particular theory, it is believed that the swelled pyrene-PEI three-dimensional networks are highly porous and facilitate the analyte (e.g. NAC molecules) to diffuse into the cavities of the swelled polymer for enhanced sensing performance. The ultrasonicated pyrene-PEI suspension is stable, indicating that pyrene-PEI may exist as ultrafine aggregates.

Example 2

Formation of a Tetryl/Pyrene-PEI Complex

The pyrene/amine hybrid configuration in pyrene-PEI allows for the potential for ultra-sensitive detection of nitroaromatic explosives through FRET-based quenching as well as PET. NACs are electron-deficient due to the high substitution of nitro groups on their aromatic rings. They have a strong charge-transfer interaction with the electron-rich amine groups and can, therefore, form deep colored Meisenheimer complexes. The strong complexing interaction between pyrene-PEI and nitroaromatic explosives is demonstrated using Tetryl as a model analyte.

Tetryl does not absorb any visible light in aqueous solution. After adding Tetryl into pyrene-PEI suspension, two new visible absorbance peaks appeared at 448 nm and 519 nm (FIG. 4b, black solid line), meanwhile, the color of solution changed from colorless to red (inset 1 of FIG. 4b). The new peak intensity and the color of solution became stronger with the increase of Tetryl concentration. These results show the formation of Tetryl-amine Meisenheimer complex (FIG. 4a) in pyrene-PEI solution.

The visible absorbance of the Tetryl-amine Meisenheimer complex greatly overlaps with the broad excimer band of pyrene-PEI centered at 470 nm (red dot line in FIG. 4a), suggesting that pyrenyl units in pyrene-PEI polymer could be the energy donor and the Tetryl-amine complex is able to act as the energy acceptor in FRET. Accordingly, the fluorescence emission of pyrene-PEI may be strongly absorbed by the Tetryl-amine complex, as shown in the inset 2 of FIG. 4b.

Figure 6:
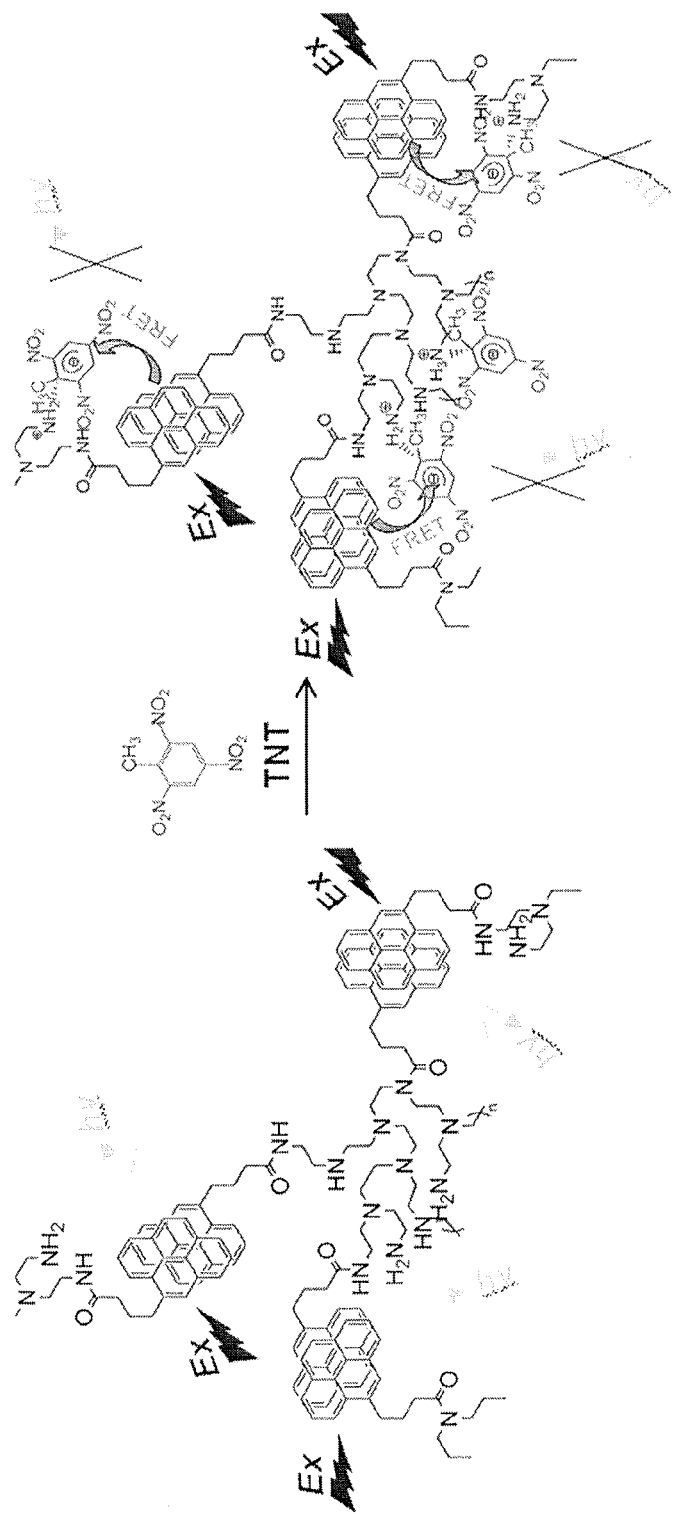
FIG. 6 shows one embodiment of the FRET quenching mechanism at the excimer peak (475 nm) of a pyrene-PEI for NACs (e.g. TNT) sensing.

Without wishing to be bound by any particular theory, it is believed that the mechanism of FRET may be interpreted well by Förster theory. The transfer efficiency E, defined as the fraction of donor that is de-excited by energy transfer to the acceptor, depends on the spectral overlap of the donor emission and the acceptor absorption, and the distance between the donor and the acceptor. For a chosen donor-acceptor pair, the FRET efficiency is given by equation $E=R_0^6/(R_0^6+r^6)$, where r is the distance between a donor and an acceptor, and $R_0$ is the Förster critical radius (for commonly used fluorophores, $R_0$ varies from 10 Å to more than 50 Å). The sixth power dependence illustrates the FRET is highly dependent on the donor-acceptor distance, and the energy transfer would be most efficient when the spatial proximity of donor and acceptor molecules could be achieved in a practical FRET system. In the synthesis of pyrene-PEI, the aminolysis reaction may be conducted with excessive amine groups, which is used to form the hybrid pyrene/amine polymer and allows sufficient amine groups for NACs as well as the NAC-amine complex adequately close to pyrenyl units. Thus the FRET-based fluorescence quenching could be spatially favourable. FIG. 6 illustrates the FRET quenching mechanism in the hybrid pyrene/amine polymer for TNT detection. TNT may be bound to amines and form Meisenheimer complexes with spatial proximity to pyrenyl units. When the excited-state electrons of the pyrenyl units return to the ground state, the released energy may be efficiently absorbed by TNT-amine, resulting in the "superior quenching".

Example 3

Fluorescence Quenching of a TNT/Pyrene-PEI Complex

The application of latent FRET polymer for various nitroaromatic explosives was investigated. When NACs are injected into a pyrene-PEI suspension, the strong complexing effect between NACs and amines may lead to the formation of NAC-amine complex. In addition, NACs may serve as weak acids and donate protons to the basic amines, and such acid-base pairing interactions may further increase the binding affinity of NACs with amines in pyrene-PEI system. The bound NACs may lead to the quenching of spatially closed pyrenyl units, however, with different quenching mechanisms for the monomer and excimer emission bands of pyrenyl units. The quenching mechanism of monomer bands may be common PET from excited-state electrons of 376/396 nm bands to the LUMO of the NAC-amine complex at 448 nm and 519 nm due to the lack of overlapping between the absorption spectrum of NACs-amine and the emission spectra of pyrene monomer. On the other hand, the quenching of pyrenyl excimer band (475 nm) may involve in both FRET and PET, and these two quenching pathways are competitive with FRET as the dominant pathway.

Figure 7:
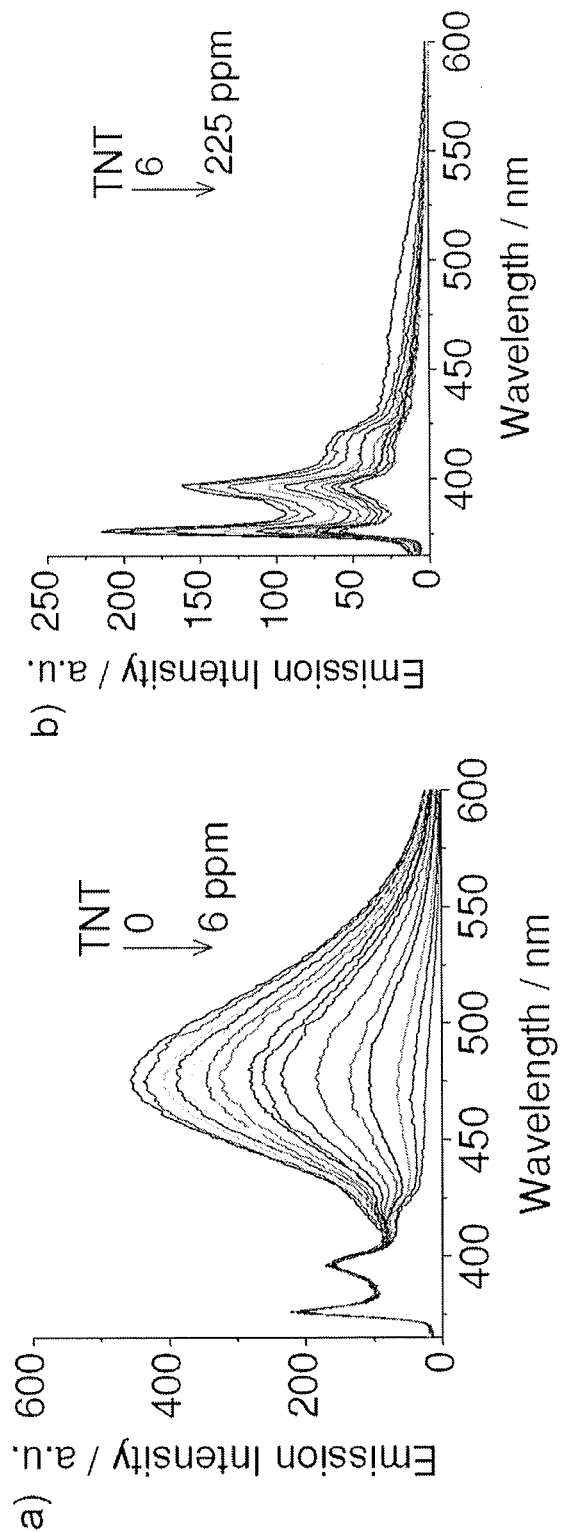
FIG. 7 shows fluorescence quenching spectra of a pyrene-PEI suspension upon titration with increasing concentrations of TNT at excitation wavelength of 343 nm.

The fluorescence quenching spectra of a pyrene-PEI suspension was collected at different TNT concentrations using an excitation wavelength of 343 nm. Ultra-trace TNT analysis was performed using concentrations of 0, 0.033, 0.164, 0.322, 0.643, 1.91, 3.44, 6.54, 18.8, 33.6, 63.7, 182.29, 327, 619, 1771, 3174, and 6014 ppb. Moderate to high concentration TNT analysis was performed using concentrations of 6.014, 17.2, 30.9, 57.1, 81.9, 105, 128, 149, 169, 189, 207, and 225 ppm. FIG. 7 shows the fluorescence quenching response of pyrene-PEI towards TNT in solution. Unlike commonly reported pyrene-based PET quenching simultaneously at both the monomer and excimer peaks, the developed hybrid pyrene-PEI polymer only shows the quenching at the excimer peak of 475 nm when trace amount of TNT was injected (FIG. 7a). Until the excimer peak was completely quenched through FRET, the monomer peaks (376 nm and 396 nm) started to be quenched upon further addition of TNT through PET (FIG. 7b). The order of fluorescence quenching at different wavelengths for TNT is 475 nm>>376 nm 396 nm due to different quenching mechanism.

FRET-amplified quenching response was obtained at substantially low concentration of NACs in pyrene-PEI suspension. The binding of NACs with amines and its resulted FRET quenching is rapid and may take less than about 1 min from the injection of analytes to completion of detection to generate distinguishable results. As shown in FIG. 7a, the emission band at 470 nm decreases with successive additions of TNT, and the fluorescence quenching can be clearly discerned at a TNT level as low as 33 ppt. The corresponding calibration curve (FIG. 8a) shows that 3.2 ppm TNT could result in 90% quenching of the pyrene-PEI emission peak at 470 nm. This sensitivity is comparable to other more complicated explosives sensors, such as those using immunoassay and Surface Plasmon Resonance. These sensor require complicated fabrication/operation procedures and/or longer detection time. The present disclosure relates to a system with potential application for near real-time and ultra-trace detection of nitroaromatic explosives.

Figure 8:
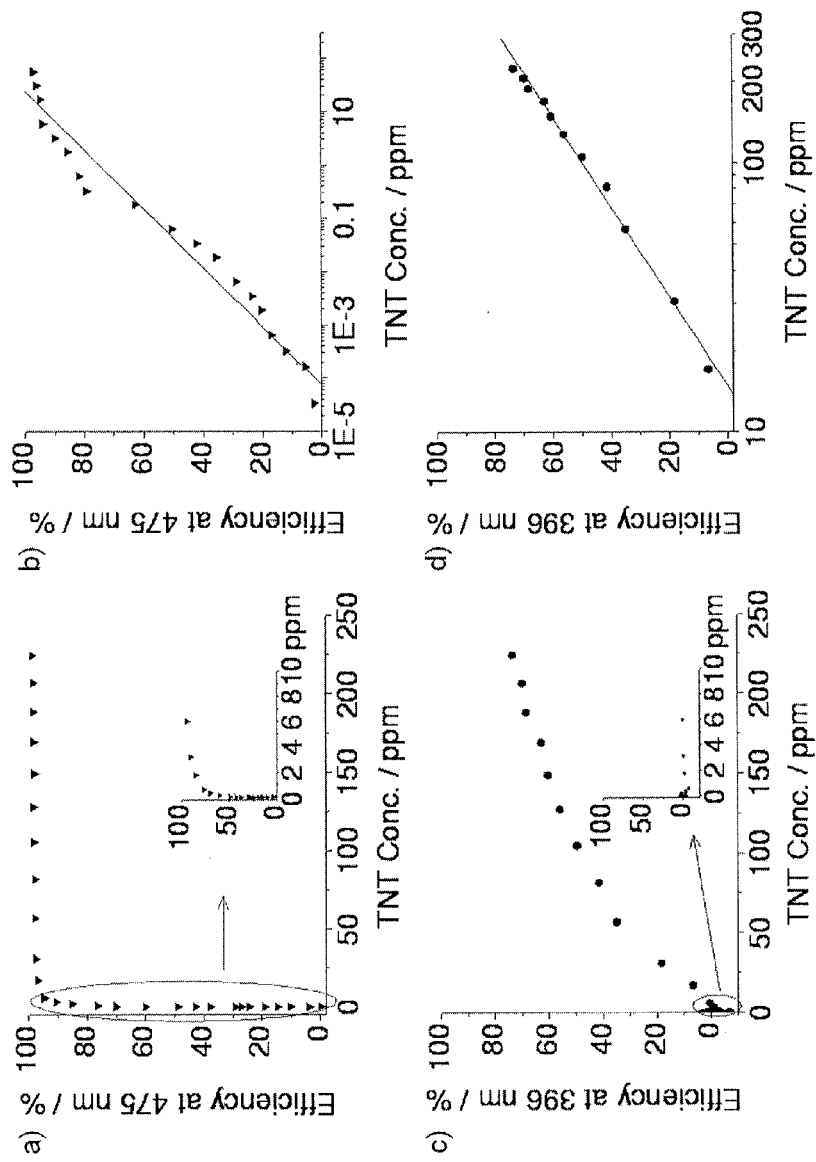
FIG. 8 shows fluorescence quenching efficiencies of a pyrene-PEI at emission bands of 475 nm (FIGS. 8a and 8b) and 396 nm (FIGS. 8c and 8d) with increasing TNT concentration from 0 to 225 ppm.
Figure 9:
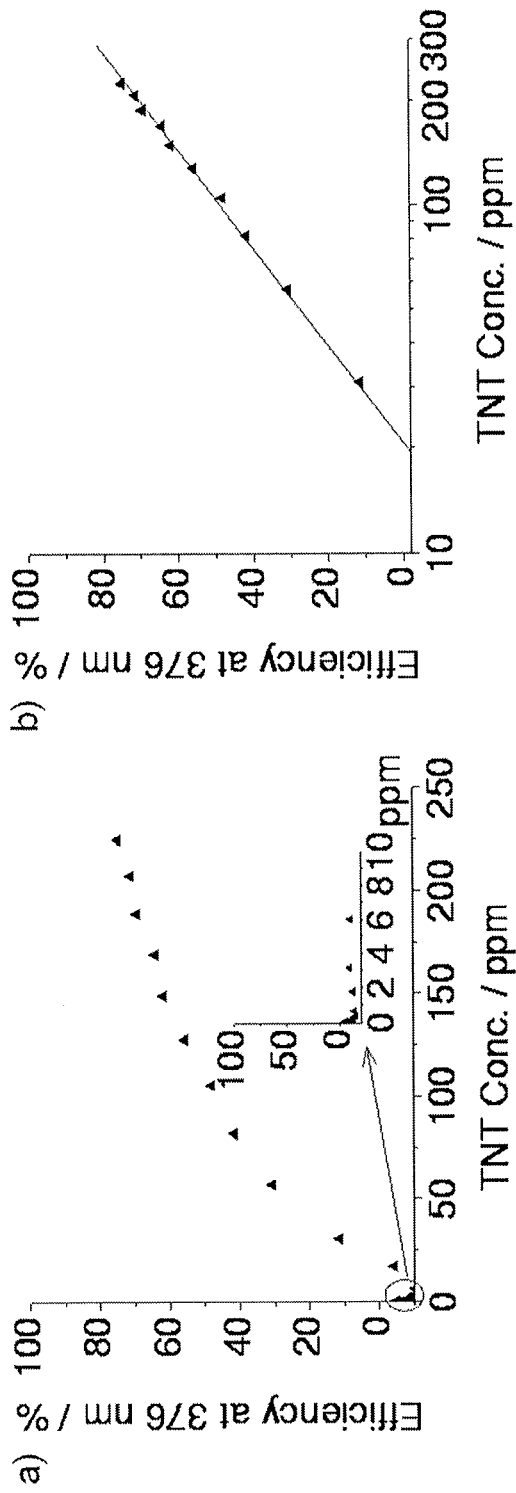
FIG. 9 shows fluorescence quenching efficiencies of a pyrene-PEI at emission bands at 376 nm with increasing TNT concentration from 0 to 225 ppm.

It is a general issue for various sensing systems that the high sensitivity and the wide sensing dynamic range need to be trade-off. However, the developed hybrid polymer may achieve a broad dynamic range for the detection of nitroaromatic explosives by taking the advantage of two quenching mechanisms (FRET and PET) in one system. The distinguishable quenching behaviour and the sequential order of fluorescence quenching at excimer band (FRET) followed by monomer bands (PET) provide a unique and feasible sensing platform for NACs detection with both ultrasensitivity and wide dynamic concentration range. FIG. 8 shows the fluorescence quenching efficiencies at the peaks of 475, 376, and 396 nm upon the addition of TNT ranging from 33 ppt to 225 ppm, spanning 7-order of magnitude. The excimer peak at 475 nm is very sensitive to trace amount of TNT (0-10 ppm), and reaches almost 100% fluorescence quenching at 10 ppm TNT (FIG. 8a). However, the monomer peaks are not quenched at those TNT concentrations, as shown in the inset of FIG. 8c. When further increasing the TNT concentration from 10 to 225 ppm, the emission at 475 nm keeps completely quenched. Surprisingly, the monomer peaks start to be gradually quenched with the increase of TNT concentration. The quenching mechanism may be ascribed to direct PET between electron-deficient NACs and electron-rich pyrene. The semi-log plots of quenching efficiency vs. TNT concentrations display good linearity from 0 to 10 ppm TNT using the quenching at the excimer peak (475 nm) through FRET (FIG. 8b), and from 10 to 225 ppm TNT using the quenching at monomer peaks (396 and 376 nm) through PET (FIG. 8d and FIG. 9). One sensing material with two sensing mechanisms may greatly enhance the detection range.

Example 4

Detection of Various Explosive Materials

Figure 10:
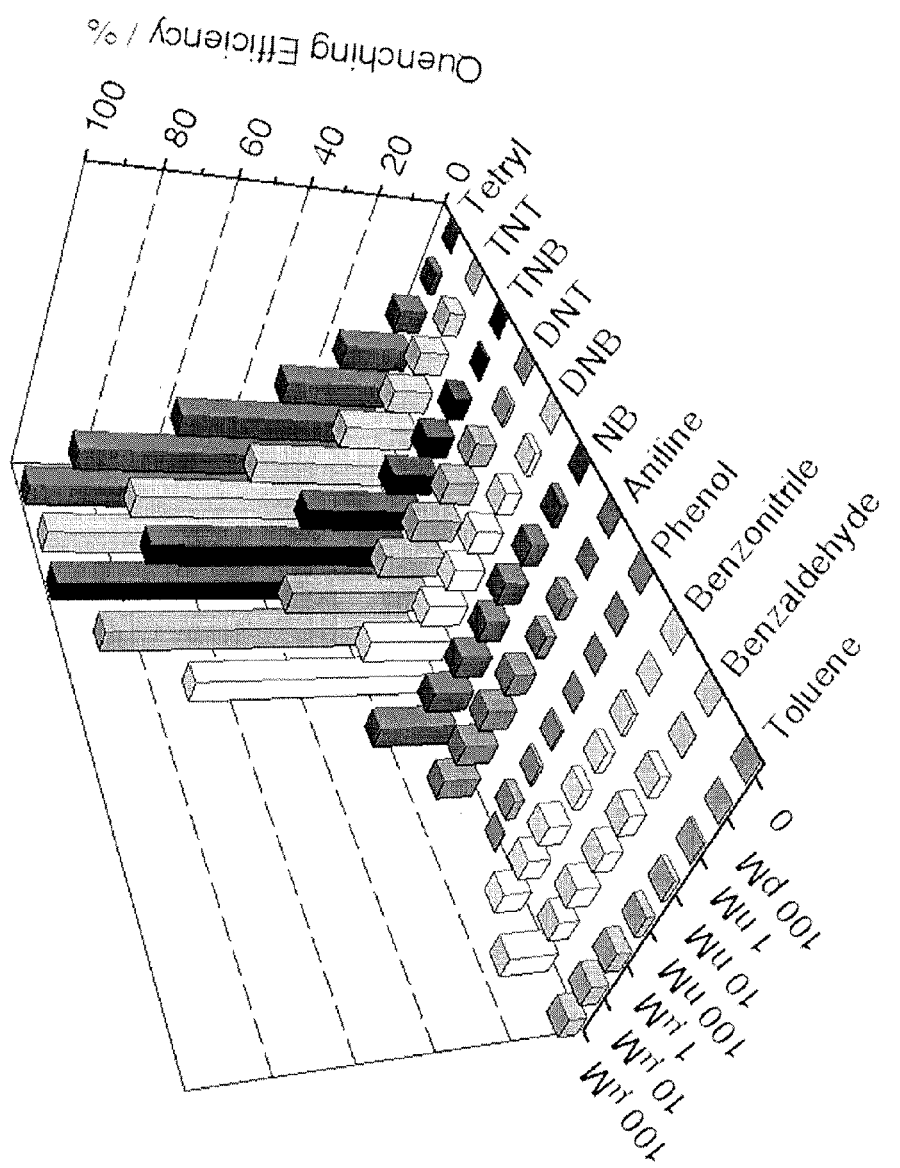
FIG. 10 shows fluorescence quenching efficiencies of a pyrene-PEI towards various nitroaromatics and common interferents.
Figure 11:
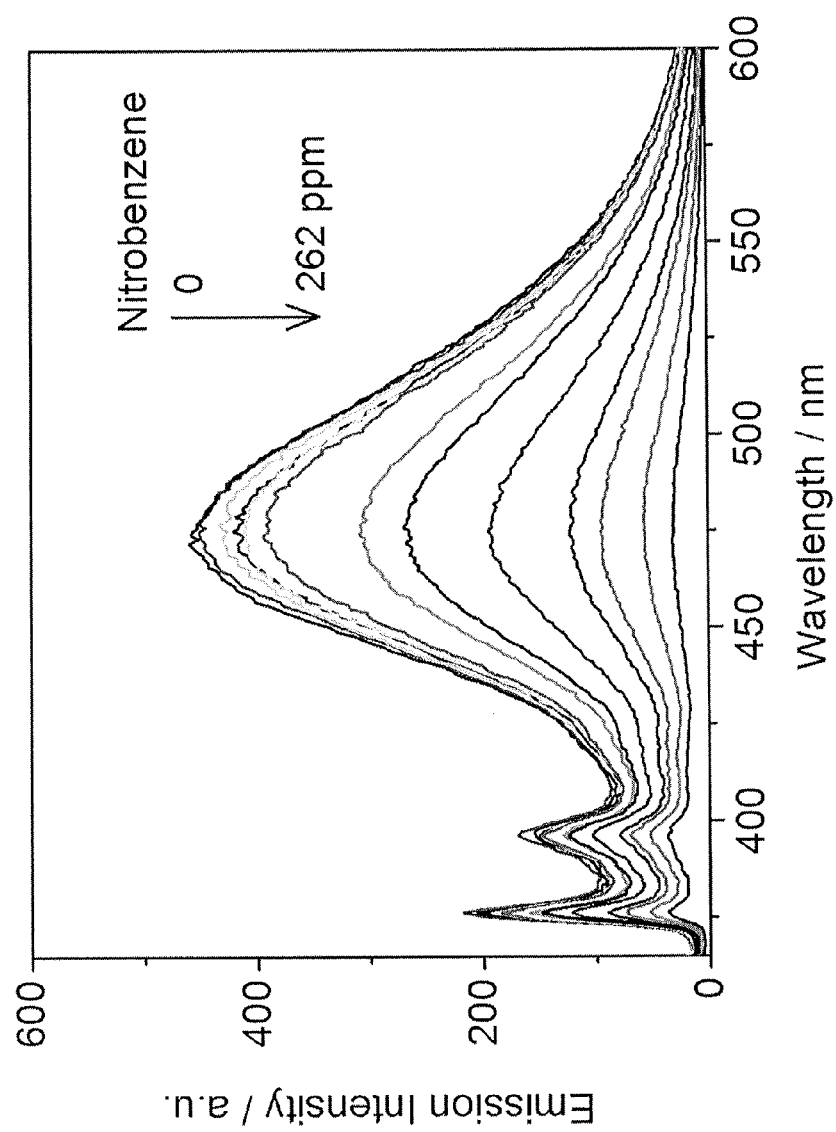
FIG. 11 shows the fluorescence quenching spectra of a pyrene-PEI solution upon titration with increasing concentrations of nitrobenzene at an excitation wavelength of 343 nm. The analyte concentrations from top to bottom are 0, 0.33, 1.32, 2.28, 3.22, 6.43, 12.8, 22.1, 34.4, 65.4, 96.3, 127, 188, and 262 ppm, respectively.

Fluorescence quenching of different nitroaromatic compounds were testing using a polymer comprising a polyamine polymer functionalized with a small molecule fluorophore. As shown in FIG. 10, Pyrene-PEI shows different fluorescence quenching degrees for different nitroaromatic explosives. Among various NAC explosives, Tetryl engendered the most sensitive quenching at the excimer peak of 475 nm. At concentrations as low as 1 µM, Tetryl addition results in 61% quenching of pyrene-PEI. This value decreases to 44%, 35%, 18%, 12%, and 9% for 1 µM solutions of TNT, trinitrobenzene (TNB), DNT, 1,3-dinitrobenzene (DNB), and nitrobenzene (NB), respectively. The different quenching efficiency in the excimer band for NACs may be a function of the variation of their electron-deficiency. Electron-deficiency is mainly determined by the number of electron-withdrawing nitro groups ($-NO_2$) on/near the aromatic ring. Tetryl possesses a large number of nitro groups, making it more electron-deficient than other NACs tested. Tetryl, therefore, may have a much stronger interaction with amine groups to form the Meisenheimer complex. Consequently, the higher degree of fluorescence quenching is achieved through FRET. NB is less electron-deficient and may have less strong interaction with amine groups to form Meisenheimer complexes. Thus, NB exhibits less dominant FRET quenching of pyrene-PEI than that in Tetryl, as evidenced by the PET-based quenching of monomer band (376 and 396 nm) starting before the excimer band was completely quenched (See FIG. 11). These results indicate the potential capability of the engineered latent FRET-PET combo system for the differentiation of structure-closely related nitroaromatic explosives.

Example 5

Selectivity of Analyte/Pyrene-PEI Complex

One of the advantages of the polymer comprising a polyamine polymer functionalized with a small molecule fluorophore is the selectivity against other electron-neutral and electro-rich aromatic compounds. Sensing experiments to investigate the interference from these compounds, such as toluene, benzaldehyde, benzonitrile, phenol, and aniline, were performed. As shown in FIG. 10, electron-neutral or electro-rich compound (e.g. toluene and phenol) fail to give any observable quenching of pyrene-PEI. It is believed this is because there is neither PET nor FRET playing a role. Electron deficient non-nitro aromatics (e.g. benzonitrile and benzaldehyde) did induce fluorescence quenching of pyrene-PEI to small degree, but with much lower efficiency compared with those of NACs. The lower quenching efficiency may be due to the lack of Meisenheimer complex and the corresponding FRET mechanism. These results indicate the good selectivity of the polymer comprising a polyamine polymer functionalized with a small molecule fluorophore.

Example 6

Sensors Comprising Pyrene-PEI Polymer

The polymer comprising a polyamine polymer functionalized with a small molecule fluorophore may be incorporated into or on a portable sampling or testing sensor, e.g. a test strip. These sensors address a long-standing need for a fast, simple, accurate way to detect explosives, such as nitroaromatic compounds, in salt water, fresh water and other liquids. The use of sensors may involve on-site sampling and sending the sensor to a laboratory for testing, or on-site sampling and testing. Prior to testing, the sample may be concentrated because water currents can dilute the explosive.

The sensor will be able to detect small amount of explosives in water samples. Sampling will be performed by dipping the sensor into a water sample, e.g. groundwater, seawater, liquid container. The sensor will be placed into an instrument to read the fluorescence and detect the presence of explosives in real-time. For high explosive concentrations, the color change of the polymer can also be used to detect explosives.

A test strip sensor was prepared by incorporating a polymer comprising a polyamine polymer functionalized with a small molecule fluorophore, as described in the present disclosure, onto a test strip. An aliquot of the polymer solution prepared in Example 1 was transferred and deposited on a paper test strip by pipette or by a screen printer. The polymer was allowed to dry prior to testing.

Figure 12:
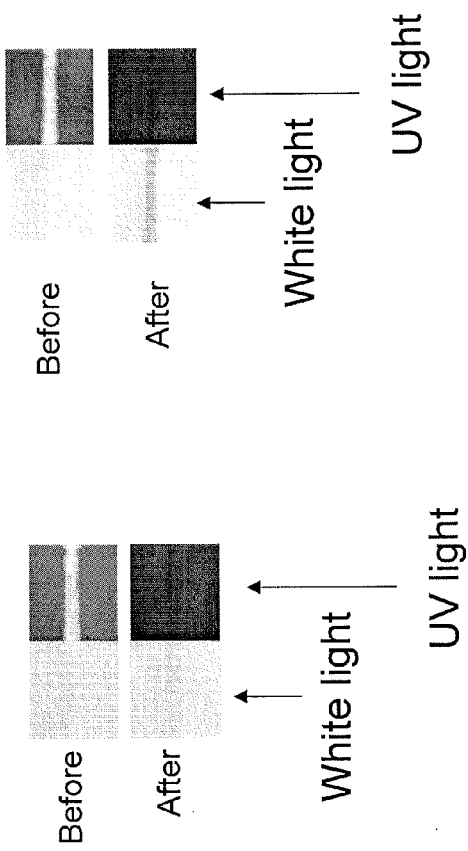
FIG. 12 shows the detection of TNT and Tetryl in solution (1000 μg/mL) using the printed test strip.

Two different explosives test solutions were prepared in solvent (e.g. acetonitrile or water). One solution contained about 1000 μg/mL (ppm) of TNT. The other solution contained about 1000 μg/mL (ppm) of Tetryl. The test strips were dipped in the solutions and readily produced a color change as well as the fluorescence quenching. FIG. 12 shows the detection of each explosive using the printed test strips.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. An explosives detecting polymer comprising a polyamine polymer covalently bonded to an organic small molecule fluorophore.

2. The polymer of claim 1, wherein the organic small molecule fluorophore comprises an aromatic multi-ring hydrocarbon, an aromatic multi-ring heterocycle, or a mixture thereof.

3. The polymer of claim 1, wherein the polyamine polymer is selected from the group consisting of polyethylenimine, polyvinyl amine, polyallylamine and polylysine.

4. The polymer of claim 1, wherein the polyamine polymer covalently bonded to an organic small molecule fluorophore comprises a plurality of structural units corresponding to Formula (I):

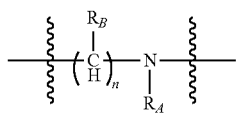

(I)

wherein each $R_A$ is selected independently from the group consisting of Formula (II) and Formula (III):

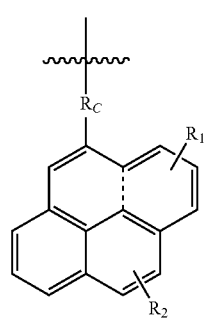

(II)

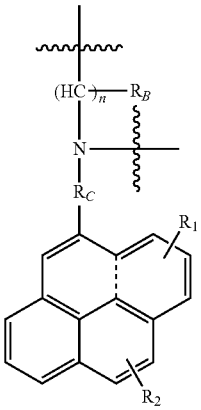

(III)

wherein each $R_C$ is selected independently from the group consisting of hydrogen and —C(O)—$C_{2-6}$ alkyl-;

wherein $R_1$ and $R_2$ are each independently selected from hydrogen, cyano, $C_{1-4}$ alkyl, —B(OH)$_2$, —C(O)H, —$C_{1-4}$ alkyl-C(O)H, —C(O)CH$_3$, —$C_{1-4}$ alkyl-C(O)CH$_3$, —C(O)OH, —$C_{1-4}$ alkyl-C(O)OH, —C(O)OCH$_3$, —$C_{1-4}$ alkyl-C(O)OCH$_3$ and —$C_{1-4}$ alkyl-C(O) O-succinimide;

$R_B$ is selected from the group consisting of a bond, hydrogen, amine and $C_1$—$C_3$ alkyl; and each n is selected independently from 2-8.

5. The polymer of claim 4, wherein $R_C$ is a hydrogen or —C(O)—$C_{2-4}$ alkyl-;

$R_B$ is selected from the group consisting of a bond and hydrogen; and each n is selected independently from 2-6.

6. The polymer of claim 4, wherein $R_C$ is hydrogen or —C(O)—$C_3$ alkyl-;

$R_B$ is hydrogen; and n is 2, 3 or 6.

7. The polymer of claim 1, wherein the organic small molecule fluorophore is selected from the group consisting of pyrene, 1-pyrenebutyric acid, pyrene-1-boronic acid, 1-pyrenebutyric acid N-hydroxysuccinimide ester, 5-carboxy-2,7-dichlorofluorescein; 5-Carboxyfluorescein (5-FAM); 5(6)-carboxyfluorescein-N-hydroxysuccinimide ester (C1609); 5-HAT (Hydroxy Tryptamine); 5-Hydroxy Tryptamine (HAT); 6-Carboxyrhodamine 6G; Acriflavin; AmCyan; Astrazon Orange R; Aurophosphine; Beta Lactamase; Bodipy 492/515; Bodipy 500/510; Bodipy Fl; Bodipy FL ATP; Bodipy Fl-Ceramide; Brilliant Sulphoflavin FF; Calcein; Calcium Green; Calcium Green-1 Ca$^{2+}$Dye; Calcium Green-2 Ca$^{2+}$; Calcium Green-5N Ca$^{2+}$; Calcium Green-C18 Ca$^{2+}$; cyclic AMP Fluorosensor (FiCRhR); Dansyl Amine; Dansyl Cadaverine; Dansyl Chloride; DCFH (Dichlorodihydrofluorescein Diacetate); DHR (Dihydrorhodamine 123); Dichlorodihydrofluorescein Diacetate (DCFH); Dihydrorhodamine 123 (DHR); DiO DiOC (3)); Dopamine; Eosin; Euchrysin; FITC Antibody; Fluo-3; Fluo-4; Fluorescein-EX; Fluorescein Diacetate; Fluoro-Emerald; Fluoro-Gold (Hydroxystilbamidine); FluorX; Fura-2, high calcium; Fura-2, low calcium; Hydroxystilbamidine (FluoroGold); Hydroxytryptamine; Lucifer Yellow; Lyso Tracker Blue-White; Lyso Tracker Green; Lyso Tracker Red; LysoSensor Green; LysoSensor Yellow/Blue; Mag Green; Mag-Fura-2; Mag-Fura-5; Magnesium Green; Monobromobimane (mBBr-GSH); Nitrobenzoxadiazole; Noradrenaline; Nylosan Brilliant lavin E8G; Oregon Green; Oregon Green 488-X; Primuline; Pyronine; Qdot 525 nanocrystal; Quinacrine Mustard; Rhodamine 110; Rhodamine 123; Rhodamine Green; Sapphire GFP; Serotonin; Sevron Orange; Sodium Green; SpectrumGreen; Tetracycline; Thiazole Orange; Thioflavin 5; Thioflavin S; Uranine B; and mixtures thereof.

8. The polymer of claim 1, wherein the organic small molecule fluorophore comprises pyrene.

9. The polymer of claim 1, wherein the polyamine polymer functionalized with a small molecule fluorophore is branched polyethylenimine functionalized with 1-pyrenebutyric acid.

10. The polymer of claim 1, wherein the small molecule fluorophore is substantially evenly distributed throughout the polymer.

11. The polymer of claim 1, wherein the small molecule fluorophore is present in the polymer at about 1% to about 60%, by molar ratio of organic small molecule fluorophore to primary amine.

12. The polymer of claim 1, wherein the polymer is capable of detecting an explosive material in an amount less than about 33 ppt.

13. The polymer of claim 1, wherein the polymer is capable of detecting an explosive material in less than about 6 minutes.

14. A method for detecting an explosive material, the method comprising:
contacting the explosives detecting polymer of claim 1 with an explosive material for at least about 1 second;
measuring an amount of fluorescence emitted by the explosives detecting polymer; and
comparing the amount of fluorescence with a control material that does not contain explosive material;
wherein an explosive material is detected where the fluorescence of the explosives detecting polymer is less than the fluorescence of the suitable control.

15. The method of claim 14, wherein the explosive material comprises at least one explosive selected from the group consisting of
octahydro-1,3,5,7-tetranitro-1,3,5,7-tetrazocine (HMX),
hexahydro-1,3,5-trinitro-1,3,5-triazine (RDX),
1,3,5-trinitrobenzene (TNB),
1,3-dinitrobenzene (DNB),
methyl-2,4,6-trinitrophenylnitramine (Tetryl),
nitrobenzene (NB),
2,4,6-trinitrotoluene (TNT),
picric acid (PA),
2,4-dinitrotoluene (24DNT),
2,6-dinitrotoluene (26DNT),
o-nitrotoluene (2NT),
m-nitrotoluene (3NT),
p-nitrotoluene (4NT),
nitroglycerin (NG),
4-amino-2,6-dinitrotoluene (4-Am-DNT),
2-amino-4,6-dinitrotoluene (2-Am-DNT),
pentaerythritol tetranitrate (PETN), and
2,3-dimethyl-2,3-dinitrobutane (DMNB).

16. The method of claim 14, wherein the method is capable of detecting an explosive material in an amount less than about 33 ppt.

17. The method of claim 14, wherein the explosive material comprises at least one explosive selected from the group consisting of
methyl-2,4,6-trinitrophenylnitramine (Tetryl),
2,4,6-trinitrotoluene (TNT),
1,3,5-trinitrobenzene (TNB),
2,4-dinitrotoluene (24DNT),
2,6-dinitrotoluene (26DNT),
1,3-dinitrobenzene (DNB), and
nitrobenzene (NB).

18. The method of claim 14 wherein measuring the amount of fluorescence emitted by the explosives detecting polymer comprises measurement of emission with a fluorimeter.

19. A sensor comprising the explosives detecting polymer of claim 1.

20. The sensor of claim 19, further comprising a complementary analytical device.

21. The sensor of claim 20, wherein the complementary analytical device is selected from the group consisting of a fluorimeter, a mass spectrometer, UV light and an absorption spectrometer.

22. A method for forming a polyamine polymer covalently bonded to an organic small molecule fluorophore, the method comprising:
providing a polyamine polymer having a structure corresponding to Formula (I):

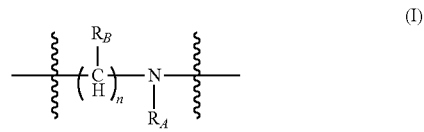

wherein each $R_A$ is selected independently from the group consisting of a repeating structure corresponding to Formula (I);
$R_B$ is selected from the group consisting of a bond, hydrogen, amine and $C_1$-$C_3$ alkyl; and
n is 2-8; and
reacting the polyamine polymer with an ester having a structure corresponding to Formula (IV):

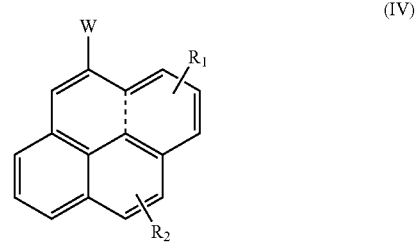

wherein W is —$C_{2-6}$ alkyl-C(O)-LG,
wherein LG is a leaving group, and
wherein $R_1$ and $R_2$ are each independently selected from hydrogen, cyano, $C_{1-4}$ alkyl, —B(OH)$_2$, —C(O)H, —$C_{1-4}$ alkyl-C(O)H, —C(O)CH$_3$, —$C_{1-4}$ alkyl-C(O)CH$_3$, —C(O)OH, —$C_{1-4}$ alkyl-C(O)OH, —C(O)OCH$_3$, —$C_{1-4}$ alkyl-C(O)OCH$_3$ and —$C_{1-4}$ alkyl-C(O)O-succinimide;
wherein the polyamine covalently bonded to an organic small molecule fluorophore is formed.

* * * * *